(12) United States Patent
Toume et al.

(10) Patent No.: US 10,792,011 B2
(45) Date of Patent: Oct. 6, 2020

(54) SYSTEMS AND METHODS FOR HAND-FREE CONTINUOUS ULTRASONIC MONITORING

(71) Applicant: Hemonitor Medical Ltd., Haifa (IL)

(72) Inventors: Samer Toume, Haifa (IL); Tom Mayblum, Tel-Aviv (IL); Avinoam Bar-Zion, Haifa (IL)

(73) Assignee: Hemonitor Medical Ltd., Haifa (IL)

( * ) Notice: Subject to any disclaimer, the term of this patent is extended or adjusted under 35 U.S.C. 154(b) by 0 days.

(21) Appl. No.: 16/474,075

(22) PCT Filed: Dec. 14, 2017

(86) PCT No.: PCT/IB2017/057932
§ 371 (c)(1),
(2) Date: Jun. 27, 2019

(87) PCT Pub. No.: WO2018/122661
PCT Pub. Date: Jul. 5, 2018

(65) Prior Publication Data
US 2019/0365348 A1    Dec. 5, 2019

Related U.S. Application Data

(63) Continuation-in-part of application No. 15/390,792, filed on Dec. 27, 2016, now Pat. No. 10,610,193,
(Continued)

(51) Int. Cl.
*A61B 8/00* (2006.01)
*A61B 8/06* (2006.01)
*A61B 8/08* (2006.01)

(52) U.S. Cl.
CPC ............ *A61B 8/4236* (2013.01); *A61B 8/065* (2013.01); *A61B 8/0891* (2013.01); *A61B 8/4272* (2013.01);
(Continued)

(58) Field of Classification Search
CPC ...... A61B 8/4236; A61B 8/065; A61B 8/0891
See application file for complete search history.

(56) References Cited

U.S. PATENT DOCUMENTS

| 5,487,388 A | 1/1996 | Rello et al. |
| 5,598,845 A | 2/1997 | Chandraratna et al. |
| (Continued) | | |

FOREIGN PATENT DOCUMENTS

| WO | WO 2012/101511 | 8/2012 |
| WO | WO 2016/207889 | 12/2016 |
| WO | WO 2018/122661 | 7/2018 |

OTHER PUBLICATIONS

Official Action dated Sep. 6, 2019 From the US Patent and Trademark Office Re. U.S. Appl. No. 15/390,792. (19 pages).
(Continued)

*Primary Examiner* — Joseph M Santos Rodriguez

(57) ABSTRACT

There is provided an assembly for hands-free ultrasonic monitoring and imaging via a suprasternal notch of a target individual, comprising: a cradle comprising: a lower portion having a surface shaped according to a surface of an anatomical region including a suprasternal notch of sample individual(s), and a holding portion connected to the lower portion, the holding portion shaped to fit a housing component, the holding portion including at least one elongated slot elongated at a predefined angle relative to the surface of the lower portion, and a housing component comprising: an ultrasound transducer, a multi-directional mechanism for adjusting the position of the ultrasound transducer within the housing component along at least two degrees of freedom, and a securing mechanism set at a location within housing component for engaging the at least one elongated slot of the cradle when housing component is fitted within the holding portion of the cradle.

19 Claims, 15 Drawing Sheets

Related U.S. Application Data which is a continuation-in-part of application No. PCT/IL2016/050664, filed on Jun. 22, 2016.

(60) Provisional application No. 62/183,278, filed on Jun. 23, 2015.

(52) U.S. Cl.
CPC ........... *A61B 8/4427* (2013.01); *A61B 8/4483* (2013.01); *A61B 8/488* (2013.01); *A61B 8/5223* (2013.01); *A61B 8/54* (2013.01)

(56) References Cited

U.S. PATENT DOCUMENTS

| | | | |
|---|---|---|---|
| 5,722,411 | A | 3/1998 | Suzuki et al. |
| 5,844,140 | A | 12/1998 | Seale |
| 6,059,727 | A | 5/2000 | Fowlkes et al. |
| 6,131,459 | A | 10/2000 | Seale et al. |
| 6,425,865 | B1 | 7/2002 | Salcudean et al. |
| 6,599,256 | B1 | 7/2003 | Acker et al. |
| 6,682,483 | B1 | 1/2004 | Abend et al. |
| 6,719,698 | B2 | 4/2004 | Manor et al. |
| 8,235,903 | B2 | 8/2012 | Abraham |
| 2004/0059220 | A1 | 3/2004 | Mourad et al. |
| 2011/0230764 | A1 | 9/2011 | Baba et al. |
| 2013/0165783 | A1 | 6/2013 | Kim et al. |
| 2013/0204127 | A1 | 8/2013 | Hoogi et al. |
| 2014/0107435 | A1 | 4/2014 | Sharf et al. |
| 2014/0114194 | A1 | 4/2014 | Kanayama et al. |
| 2014/0378835 | A1 | 12/2014 | Satoh et al. |
| 2017/0105700 | A1 | 4/2017 | Bar-Zion et al. |
| 2019/0046158 | A1 | 2/2019 | Kroon et al. |

OTHER PUBLICATIONS

International Search Report and the Written Opinion dated Apr. 15, 2018 From the International Searching Authority Re. Application No. PCT/IB2017/057932. (12 Pages).

International Search Report and the Written Opinion dated Sep. 29, 2016 From the International Searching Authority Re. Application No. PCT/IL2016/050664. (11 Pages).

Official Action dated Mar. 7, 2019 From the US Patent and Trademark Office Re. U.S. Appl. No. 15/390,792. (19 Pages).

Restriction Official Action dated Oct. 18, 2018 From the US Patent and Trademark Office Re. U.S. Appl. No. 15/390,792. (6 pages).

SYSTEMS AND METHODS FOR HAND-FREE CONTINUOUS ULTRASONIC MONITORING

RELATED APPLICATIONS

This application is a National Phase of PCT Patent Application No. PCT/IB2017/057932 having International filing date of Dec. 14, 2017, which is a Continuation-in-Part (CIP) of U.S. patent application Ser. No. 15/390,792 filed on Dec. 27, 2016, which is a Continuation-in-Part (CIP) of PCT Patent Application No. PCT/IL2016/050664 having International filing date of Jun. 22, 2016, which claims the benefit of priority under 35 USC § 119(e) of U.S. Provisional Patent Application No. 62/183,278 filed on Jun. 23, 2015. The contents of the above applications are all incorporated by reference as if fully set forth herein in their entirety.

FIELD OF THE INVENTION

The present invention relates to ultrasonic monitoring. More particularly, the present invention relates to continuous ultrasonic monitoring.

BACKGROUND OF THE INVENTION

Fluid management is typically required for all intensive care unit (ICU) patients. In the case of critically ill patients, fluid management is an important and difficult issue. Fluid resuscitation is an initial therapeutic intervention with patients after suffering a trauma, or when symptoms of hypotension, evidence of poor organ/tissue perfusion, or other significant hemodynamic challenges are present. Fluid resuscitation refers to the medical practice of replenishing body fluids lost through perspiration, bleeding, fluid shifts, or other pathological processes. The replenishing may include introduction of fluids orally, intravenously, or otherwise.

In some cases, suboptimal administration of fluid resuscitation may lead to an increase in morbidity and mortality in critically ill patients. Therefore, fluid management, in which fluid resuscitation is coordinated with hemodynamic monitoring, is an important component of the treatment of patients requiring fluid resuscitation. Various types of hemodynamic monitors may provide physicians with measurements of various hemodynamic parameters. Such parameters may include stroke volume (the volume of blood that is pumped from the left ventricle during each heartbeat), heart rate, cardiac output, respiration rate, or other relevant hemodynamic parameters. Knowledge of the values of such parameters may assist a physician in determining whether or not fluid resuscitation is necessary, and if it is, what quantity of fluid is to be administered.

The hemodynamic monitors that are most widely used are invasive devices. For example, an invasive device may include one or more catheters or sensors that are inserted into the patient's blood vessels.

Ultrasound imaging is widely used as a tool for medical diagnostics. Ultrasound imaging may provide high-resolution images of internal organs and biological structures deep inside the body, as well as functional information, e.g., with regard to cardiac function and blood flow. A typical ultrasound transducer includes an array of elements that emit and receive ultrasonic waves. When operated in brightness mode (B-mode), an ultrasound system may generate real time two-dimensional images based on the received waves. When operated in Doppler mode, the ultrasound system may provide measurements of the velocities of blood and tissue. Doppler ultrasound may be used to estimate blood velocity by transmitting streams of high-frequency sound waves and analyzing the signals reflected from circulating red blood cells. The local velocity profile is derived from measured changes in the phase of a received signal. Doppler scans may be used in the diagnosis of such conditions as heart valve defects, congenital heart disease, artery occlusions, and aneurysms.

SUMMARY OF THE INVENTION

According to a first aspect, an assembly for hands-free ultrasonic monitoring and imaging of at least one target anatomical structure via a suprasternal notch of a target individual, comprises: a cradle comprising: a lower portion having a surface shaped according to a surface of an anatomical region including a suprasternal notch of at least one sample individual, and a holding portion connected to the lower portion, the holding portion shaped to fit a housing component, the holding portion including at least one elongated slot elongated at a predefined angle relative to the surface of the lower portion, and a housing component comprising: an ultrasound transducer, a multi-directional mechanism for adjusting the position of the ultrasound transducer within the housing component along at least two degrees of freedom, and a securing mechanism set at a location within housing component for engaging the at least one elongated slot of the cradle when housing component is fitted within the holding portion of the cradle.

According to a second aspect, A multi-directional mechanism for adjusting a position of an ultrasound transducer within a housing component along at least two degrees of freedom, comprising: at least one resilient element set for providing linear motion of the ultrasound transducer along a vertical axis of the housing component, wherein a first end portion of the at least one resilient element is connected to the housing component and a second end portion of the at least one resilient element is connected to the ultrasound transducer, a tilting actuator for tiling the ultrasound transducer along a roll axis arranged in parallel to a longitudinal axis of the housing compartment, a rotation actuator for rotating the ultrasound transducer along a yaw axis arranged in parallel to a vertical axis of the housing component, wherein the at least one resilient element linearly urges the tilting actuator and rotation actuator along a vertical axis of the housing component.

Images of anatomical structures, for example, the ascending aorta and/or the aortic arch may be obtained by ultrasonic imaging via the suprasternal notch. However, the surface shape of the suprasternal notch is complex, non-flat, and confined between the clavicle bones. Moreover, the surface anatomy of the suprasternal notch (and nearby surface anatomy) and/or the location of the internal anatomical structures being imaged may vary between target individuals. The assembly is designed to fit to the suprasternal notch and/or is shaped to accommodate uneven surfaces around the suprasternal notch and/or without significantly impacting the ability to move the neck.

The ultrasonic monitoring and/or imaging of one or more anatomical structures via the suprasternal notch is performed without requiring continuous holding by an operator, and/or without requiring manual adjustment of the ultrasound transducer against the skin. Once the housing is connected to the cradle, and the initial pitch and linear displacement are set, the ultrasound detection of anatomical structures and/or monitoring is performed hands-free, without a manual human operator.

The cradle provides hands-free anchoring of the ultrasound housing to the suprasternal notch (i.e., without requiring a human operator to hold the ultrasound housing in place) during an ultrasonic monitoring session. The shape of the bottom of the cradle is designed to match the shape of a suprasternal notch of the target individual (e.g., an average shape computed based on an analysis of shapes of one or more sample individuals).

The multi-directional mechanism is designed for automated and/or hands-free fine adjustment of the ultrasound transducer, optionally a phased array, along three degrees of freedom. A human operator holding the transducer in place and/or adjusting the position of the transducer is not required. The mechanism adjustment of a phased array adds additional mechanical degrees of motion, in addition to the electronic degrees of freedom of the phased array. The combination of mechanical degrees of freedom and electronic degrees of freedom provide, for example, for a larger field of view, obtaining image planes in a relatively larger number of different orientations, improved fine tuning for capturing quality ultrasound images, and/or for scanning a volume of tissue for reconstruction of three dimensional ultrasound images. Alternatively, in an implementation of a single ultrasound transducer, the mechanism adjustment of a single ultrasound transducer element may replace electrical adjustment of the beam of a phased array. The mechanism adjustment may provide for improved image quality when the single ultrasound transducer is implemented. The mechanism provides for improved sweeping of the ultrasound transducer along a volume of tissue, for example, for reconstruction of 3D ultrasound images of the volume. The improvement may be, for example, in terms of increased volume that may be imaged and/or improved image quality in comparison to the phased array.

In a further implementation form of the first and second aspects, the housing component further comprises: a pitch adjustment mechanism for adjusting a pitch of the housing component relative to the cradle, wherein the securing mechanism locks the housing component at a certain pitch, and a linear motion mechanism for adjusting a linear displacement of the housing component relative to the cradle along a linear displacement axis defined along the elongated slot.

In a further implementation form of the first and second aspects, the holding portion of the cradle is sized for providing: (i) a pitch range of the housing component above a baseline pitch substantially corresponding to a pitch of the suprasternal notch when the cradle houses the housing component in use, and (ii) a linear displacement range of motion of the housing component along a linear displacement axis of the holding portion.

In a further implementation form of the first and second aspects, the linear displacement axis is parallel to an axis defining the baseline pitch.

In a further implementation form of the first and second aspects, the pitch adjustment mechanism, the linear motion mechanism, and the securing mechanism are implemented by the elongated slot of the cradle and at least one securing element located on one or both of the sides of the housing component, wherein when the at least one securing element is tightened within the at least one elongated slot the housing component is secured within the cradle at the certain pitch and the certain linear displacement.

In a further implementation form of the first and second aspects, the linear motion mechanism is set for adjusting the position of the housing component within a range of about 10 millimeters (mm) along the linear axis.

In a further implementation form of the first and second aspects, the pitch adjustment mechanism is set for adjusting the pitch of the housing component relative to the lower surface of the lower component of the cradle.

In a further implementation form of the first and second aspects, the pitch adjustment mechanism is set for adjusting the pitch of the housing component relative to the cradle within a range of about 10-15 degrees.

In a further implementation form of the first and second aspects, the multi-directional mechanism includes at least one resilient element set for providing linear motion of the ultrasound transducer along a vertical axis of the housing component.

In a further implementation form of the first and second aspects, the at least one resilient element is set for pressing the ultrasound transducer within a compartment housing acoustic transmission material such that the ultrasound transducer maintains contact with the surface of the compartment housing acoustic transmission material during motion within the at least three degrees of motion provided by the multi-directional mechanism.

In a further implementation form of the first and second aspects, the at least one resilient element includes at least one spring having a first end portion connected to the housing component and a second end portion connected to a top surface of a flat plate, wherein the ultrasound transducer is connected to a bottom surface of the flat plate.

In a further implementation form of the first and second aspects, the at least one spring is arranged along a vertical axis of the housing component for urging the ultrasound transducer along the vertical axis.

In a further implementation form of the first and second aspects, a spring constant of the at least one spring is selected for urging the ultrasound transducer towards the suprasternal notch with a pressure requirement that provides quality ultrasound images.

In a further implementation form of the first and second aspects, the at least one resilient element is located internally within the housing component at a location corresponding to an external location of the securing mechanism located on one or both external side surfaces of the housing component.

In a further implementation form of the first and second aspects, the multi-directional mechanism includes a tilting actuator for tiling the ultrasound transducer along a roll axis arranged in parallel to a longitudinal axis of the housing compartment.

In a further implementation form of the first and second aspects, the tilting actuator is located on a bottom surface of a flat plate, wherein the top surface of the flat plate is connected to one end of at least one resilient element of the multi-directional mechanism, wherein an opposite end of the at least one resilient element is coupled to the housing, wherein the at least one resilient element linearly urges the flat plate and connected tilting actuator along a vertical axis of the housing component.

In a further implementation form of the first and second aspects, the tilting actuator is arranged in parallel to a longitudinal axis of the housing component, wherein the tilting actuator is located along the bottom of the housing component.

In a further implementation form of the first and second aspects, the tilting actuator includes a tilting micro stepper motor and a tilting motor shaft connected at a first end thereof to a support connected to the ultrasound transducer, and connected at a second end thereof to the tilting motor, wherein the support, the tilting motor shaft, and the tilting motor are arranged along a linear axis substantially parallel to the longitudinal axis of the housing component, wherein the tilting actuator tilts the ultrasound transducer by rotating the tilting motor shaft that tilts the support connected to the ultrasound transducer.

In a further implementation form of the first and second aspects, the multi-directional mechanism includes a rotation actuator for rotating the ultrasound transducer along a yaw axis arranged in parallel to a vertical axis of the housing component.

In a further implementation form of the first and second aspects, the rotation actuator includes a rotation micro stepper motor coupled to a first end portion of a rotational motor shaft, wherein a second end portion of the rotational motor shaft is coupled to a worm gear, wherein the rotation micro stepper motor, the rotational motor shaft, and the worm gear are arranged along a linear axis substantially parallel to a longitudinal axis of the housing component, wherein the worm gear is meshed to a gear of a rotational shaft coupled to a support of the ultrasound transducer, wherein the rotational motor shaft is arranged substantially parallel to a vertical axis of the housing component.

In a further implementation form of the first and second aspects, the rotation actuator is located on a top surface of a flat plate, wherein the top surface of the flat plate is connected to one end of at least one resilient element of the multi-directional mechanism, wherein an opposite end of the at least one resilient element is coupled to the housing, wherein the at least one resilient element linearly urges the flat plate and connected rotation actuator along a vertical axis of the housing component.

In a further implementation form of the first and second aspects, a rotational motor shaft extends through the flat plate to connect to the support of the ultrasound transducer.

In a further implementation form of the first and second aspects, the gear of the rotational motor shaft is located along a longitudinal mid-line of the housing component, wherein the rotation micro stepper motor, the motor shaft, and the worm gear are aligned along a longitudinal axis of the housing component located in parallel to the mid-line.

In a further implementation form of the first and second aspects, the rotation actuator is designed for providing a torque sufficient to overcome frictional forces when rotating the ultrasound transducer when the ultrasound transducer is urged by at least one resilient element towards the suprasternal notch, the torque selected to overcome frictional forces between the ultrasound transducer and a compartment of an acoustic material in contact with the suprasternal notch.

In a further implementation form of the first and second aspects, the torque is about 14 kg*cm.

In a further implementation form of the first and second aspects, the rotation actuator is set for rotating the ultrasound transducer along the yaw axis within a range of about 80 degrees. In a further implementation form of the first and second aspects, the pitch adjustment mechanism and the linear motion mechanism are manually adjustable, and the multi-directional mechanism is automatically adjustable by at least one actuator.

In a further implementation form of the first and second aspects, further comprising a set of a fixed photodiode gate and a needle defining a reference zero position for calibrating each axis of motion of the assembly, wherein motion occurring along each axis of motion is relative to the reference zero point.

In a further implementation form of the first and second aspects, the lower portion includes an adhesive for adhering to the skin of the patient at the anatomical region that includes the suprasternal notch.

In a further implementation form of the first and second aspects, the predefined angle substantially corresponds to an angle between the surface of the suprasternal notch of at least one sample individual and an angle for imaging at least one internal anatomical structure of the at least one sample individual via the suprasternal notch.

In a further implementation form of the first and second aspects, the predefined angle is selected within the range of 15 to 60 degrees.

In a further implementation form of the first and second aspects, the lower portion includes an acoustic window including an acoustic transmission material within the lower surface, the acoustic window sized to correspond to a size of the suprasternal notch of at least one sample individual.

In a further implementation form of the first and second aspects, the acoustic transmission material is enclosed in a compartment located within the acoustic window, wherein a first surface of the compartment contacts the skin of the suprasternal notch and a second surface opposite the first surface contacts the ultrasound transducer of the housing component.

In a further implementation form of the first and second aspects, the first surface of the compartment is shaped according to a surface of the suprasternal notch of at least one sample individual.

In a further implementation form of the first and second aspects, the first surface of the compartment includes an adhesive for adhering to the surface of the suprasternal notch.

In a further implementation form of the first and second aspects, the lower portion is larger than the area of the holding portion coupled to the lower portion, wherein the region of the lower portion larger than the area of the holding portion is shaped to fit the anatomical region surrounding the suprasternal notch.

In a further implementation form of the first and second aspects, the lower portion includes a plurality of slots extending from an edge of the lower portion towards the holding portion.

In a further implementation form of the first and second aspects, the lower portion includes a flexible material that matches to the shape of the body surface when pressed towards the body surface.

In a further implementation form of the first and second aspects, further comprising at least one hardware processor coupled to the multi-directional mechanism and to a data storage device storing code for execution by the at least one hardware processor, the code including instructions for controlling the multi-directional mechanism to perform a defined sweeping pattern that sweeps the ultrasound transducer for capturing a sequence of ultrasound images each representing a two dimensional slice at a certain orientation, wherein at least one three-dimensional image is reconstructed from the sequence of two dimensional ultrasound image slices and according a position and orientation of the ultrasound transducer for each two dimensional slice based on setting of the multi-directional mechanism.

In a further implementation form of the first and second aspects, further comprising at least one handle located on the exterior surface of the cradle, the at least one handle including a strap locking mechanism that secures a strap wrapped around the neck of the patient.

In a further implementation form of the first and second aspects, the at least one resilient element is connected to a top surface of a flat plate, the ultrasound transducer is connected to a bottom surface of the flat plate, wherein the tilting actuator is located on the bottom surface of the flat plate, wherein the rotation actuator is located on the top surface of the flat plate, wherein the at least one resilient element linearly urges the flat plate and connected tilting actuator and connected rotation actuator along a vertical axis of the housing component.

In a further implementation form of the first and second aspects, the at least one resilient element includes at least one spring arranged along the vertical axis of the housing component for urging the ultrasound transducer along the vertical axis.

In a further implementation form of the first and second aspects, the tilting actuator is arranged in parallel to a longitudinal axis of the housing component, wherein the tilting actuator is located along the bottom of the housing component.

In a further implementation form of the first and second aspects, the tilting actuator includes a tilting micro stepper motor and a tilting motor shaft connected at a first end thereof to a support connected to the ultrasound transducer, and connected at a second end thereof to the tilting motor, wherein the support, the tilting motor shaft, and the tilting motor are arranged along a linear axis substantially parallel to the longitudinal axis of the housing component, wherein the tilting actuator tilts the ultrasound transducer by rotating the tilting motor shaft that tilts the support connected to the ultrasound transducer.

In a further implementation form of the first and second aspects, the rotation actuator includes a rotation micro stepper motor coupled to a first end portion of a motor shaft, wherein a second end portion of the motor shaft is coupled to a worm gear, wherein the rotation micro stepper motor, the motor shaft, and the worm gear are arranged along a linear axis substantially parallel to a longitudinal axis of the housing component, wherein the worm gear is meshed to a gear of a rotational shaft coupled to a support of the ultrasound transducer, wherein the rotational shaft is arranged substantially parallel to a vertical axis of the housing component, wherein the rotational shaft extends through the flat plate to connect to the support of the ultrasound transducer.

In a further implementation form of the first and second aspects, the gear of the rotational shaft is located along a longitudinal mid-line of the housing component, wherein the rotation micro stepper motor, the motor shaft, and the worm gear are aligned along a longitudinal axis of the housing component located in parallel to the mid-line.

In a further implementation form of the first and second aspects, the rotation actuator is designed for providing a toque sufficient to overcome frictional forces when rotating the ultrasound transducer when the ultrasound transducer is urged by at least one resilient element, the torque selected to overcome frictional forces between the ultrasound transducer and a compartment of an acoustic material.

In a further implementation form of the first and second aspects, the at least one resilient element is set for pressing the ultrasound transducer within a compartment housing acoustic transmission material such that the ultrasound transducer maintains contact with the surface of the compartment housing acoustic transmission material during motion within the at least three degrees of motion provided by the multi-directional mechanism.

In a further implementation form of the first and second aspects, the ultrasound transducer includes a one dimensional phased array.

In a further implementation form of the first and second aspects, further comprising at least one hardware processor coupled to the multi-directional mechanism and to a data storage device storing code for execution by the at least one hardware processor, the code including instructions for controlling the multi-directional mechanism to perform a defined sweeping pattern that sweeps the ultrasound transducer for capturing a sequence of ultrasound images each representing a two dimensional slice at a certain orientation.

BRIEF DESCRIPTION OF THE SEVERAL VIEWS OF THE DRAWINGS

In order for the present invention, to be better understood and for its practical applications to be appreciated, the following Figures are provided and referenced hereafter. It should be noted that the Figures are given as examples only and in no way limit the scope of the invention. Like components are denoted by like reference numerals.

DETAILED DESCRIPTION OF THE INVENTION

Figure 1:
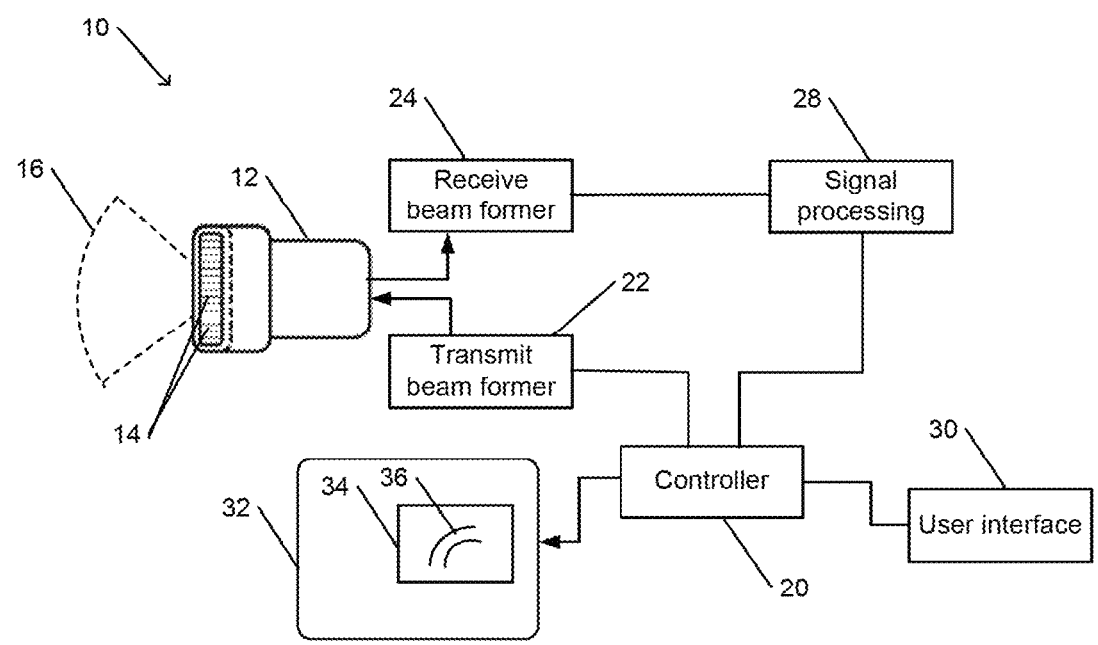
FIG. 1 shows a block diagram of a system for continuous ultrasonic monitoring, in accordance an embodiment of the present invention.

In the following detailed description, numerous specific details are set forth in order to provide a thorough understanding of the invention. However, it will be understood by those of ordinary skill in the art that the invention may be practiced without these specific details. In other instances, well-known methods, procedures, components, modules, units and/or circuits have not been described in detail so as not to obscure the invention.

Although embodiments of the invention are not limited in this regard, discussions utilizing terms such as, for example, "processing," "computing," "calculating," "determining," "establishing", "analyzing", "checking", or the like, may refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium (e.g., a memory) that may store instructions to perform operations and/or processes. Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. Unless explicitly stated, the method embodiments described herein are not constrained to a particular order or sequence. Additionally, some of the described method embodiments or elements thereof can occur or be performed simultaneously, at the same point in time, or concurrently. Unless otherwise indicated, the conjunction "or" as used herein is to be understood as inclusive (any or all of the stated options).

Some embodiments of the invention may include an article such as a computer or processor readable medium, or a computer or processor non-transitory storage medium, such as for example a memory, a disk drive, or a USB flash memory, encoding, including or storing instructions, e.g., computer-executable instructions, which when executed by a processor or controller, carry out methods disclosed herein.

An aspect of some embodiments of the present invention relates to an assembly for hands-free ultrasonic imaging and/or monitoring via a suprasternal notch of a target individual. The assembly includes a housing component storing an ultrasound transducer, optionally a single ultrasound transducer element. The housing component is designed to fit within a cradle that adheres to a skin of an anatomical region that includes the suprasternal notch of the target individual. The housing component includes a pitch adjustment mechanism and a linear motion mechanism. The pitch adjustment mechanism adjusts a pitch of the housing component relative to the cradle. The linear motion mechanism adjusts a linear displacement of the housing component relative to the cradle along a linear axis of the cradle. A multi-directional mechanism adjusts the position and/or orientation of the ultrasound transducer within the housing component along at least two degrees of freedom, optionally three degrees of freedom.

The cradle couples the housing component to an anatomical region including a suprasternal notch of a target individual, for hands-free ultrasonic imaging via the suprasternal notch. The cradle includes a lower portion that includes a surface shaped according to a surface of an anatomical region that includes the suprastrenal notch. A holding portion of the cradle is shaped to fit the housing component. The holding portion may be sized for providing for a pitch range of motion of the housing component, and a linear displacement range of motion of the housing component along a linear displacement axis of the holding portion.

Images of anatomical structures, for example, the ascending aorta and/or the aortic arch may be obtained by ultrasonic imaging via the suprasternal notch. However, the surface shape of the suprasternal notch is complex, non-flat, and confined between the clavicle bones. Moreover, the surface anatomy of the suprasternal notch (and nearby surface anatomy) and/or the location of the internal anatomical structures being imaged may vary between target individuals. The assembly is designed to fit to the suprasternal notch and/or is shaped to accommodate uneven surfaces around the suprasternal notch and/or without significantly impacting the ability to move the neck.

The pitch adjustment mechanism and the linear motion mechanism provide two degrees of freedom, in addition to the degrees of freedom of movement of the ultrasound transducer, for adjustment of the positioning of the housing according to anatomical variations of target individuals. The additional degrees of freedom provided by the pitch adjustment mechanism and/or the linear motion mechanism provide a wider scanning region for the ultrasound beam of the ultrasound transducer for searching (optionally automatically) for one or more target anatomical structures within a larger field of view through the suprasternal notch.

The ultrasonic monitoring and/or imaging of one or more anatomical structures via the suprasternal notch is performed without requiring continuous holding by an operator, and/or without requiring manual adjustment of the ultrasound transducer against the skin. Once the housing is connected to the cradle, and the initial pitch and linear displacement are set, the ultrasound detection of anatomical structures and/or monitoring is performed hands-free, without a manual human operator.

The cradle provides hands-free anchoring of the ultrasound housing to the suprasternal notch (i.e., without requiring a human operator to hold the ultrasound housing in place) during an ultrasonic monitoring session. The shape of the bottom of the cradle is designed to match the shape of a suprasternal notch of the target individual (e.g., an average shape computed based on an analysis of shapes of one or more sample individuals).

An aspect of some embodiments of the present invention relates to a multi-directional mechanism for adjusting a position and/or orientation of an ultrasound transducer within a housing component along at least two degrees of freedom, optionally three degrees of freedom. The multi-directional mechanism includes one or more resilient elements (e.g., spring(s)) set for providing linear motion of the ultrasound transducer along a vertical axis of the housing component. One end portion of the resilient element(s) is connected to the housing component. The other end portion of the resilient element(s) is connected to a top surface of a flat plate. The ultrasound transducer is connected to a bottom surface of the flat plate. The multi-directional mechanism further includes a tilting actuator (e.g., motor and/or gears) for tiling the ultrasound transducer along a roll axis arranged in parallel to a longitudinal axis of the housing compartment. The tilting actuator is located on the bottom surface of the flat plate. The multi-directional mechanism further includes a rotation actuator for rotating the ultrasound transducer along a yaw axis arranged in parallel to a vertical axis of the housing component. The rotation actuator is located on the top surface of the flat plate. The resilient element linearly urges the flat plate and connected tilting actuator and connected rotation actuator along a vertical axis of the housing component.

The multi-directional mechanism is designed for automated and/or hands-free fine adjustment of the ultrasound transducer, optionally a phased array, along three degrees of freedom. A human operator holding the transducer in place and/or adjusting the position of the transducer is not required. The mechanism adjustment of a phased array adds additional mechanical degrees of motion, in addition to the electronic degrees of freedom of the phased array. The combination of mechanical degrees of freedom and electronic degrees of freedom provide, for example, for a larger field of view, obtaining image planes in a relatively larger number of different orientations, improved fine tuning for capturing quality ultrasound images, and/or for scanning a volume of tissue for reconstruction of three dimensional ultrasound images. Alternatively, in an implementation of a single ultrasound transducer, the mechanism adjustment of a single ultrasound transducer element may replace electrical adjustment of the beam of a phased array. The mechanism adjustment may provide for improved image quality when the single ultrasound transducer is implemented. The mechanism provides for improved sweeping of the ultrasound transducer along a volume of tissue, for example, for reconstruction of 3D ultrasound images of the volume. The improvement may be, for example, in terms of increased volume that may be imaged and/or improved image quality in comparison to the phased array.

In accordance with an embodiment of the present invention, a continuous ultrasonic monitoring system is provided to continuously monitor an anatomical structure by maintaining an object within the body of a patient within an ultrasound image. For example, the object may include an anatomical structure such as an organ, blood vessel, or tumor, or a foreign object (e.g., an implanted or ingested object, or an object that is introduced into the body as a result of injury). The system includes an ultrasound measurement unit. The ultrasound measurement unit is configured to attach to the body of a patient, to transmit ultrasound pulses into the patient's body, and to receive ultrasound signals that are reflected from internal structures in the patient's body.

In particular, the ultrasound monitoring system may be utilized to continuously and non-invasively monitor stroke volume, cardiac output (blood volume per unit time, e.g., calculated by multiplying stroke volume by heart rate), stroke volume variations, systemic vascular resistance, or another hemodynamic parameter.

The ultrasound measurement unit includes an ultrasound transducer that includes an array of ultrasonic transducer elements. The system includes a beam former that may introduce phase delays between the signals that are transmitted or received by each of the ultrasonic transducer elements. The beam former may control the phases to do one or more of focus the transmitted ultrasonic beam in the plane of the array to a selectable distance from the ultrasound transducer, receive ultrasound signals from point at a selectable distance from the ultrasound transducer, to aim the ultrasound beam in a selectable direction in the plane of the array, to receive ultrasound from a selectable direction in the plane of the array, or to produce a plane wave. The ultrasonic transducer elements of the ultrasound transducer may be operated in an imaging mode (B-mode) to produce an image, or in Doppler mode to measure a velocity of a measured object or flow.

The ultrasound transducer may be attached to a part of the body of a patient so as to acquire measurements within a region of the patient's body. For example, the region may include the thoracic region or upper abdomen of the patient, or another region of the patient (e.g., the leg, neck, or another part of the body). For example, the ultrasound transducer may be attached to the suprasternal notch, upper abdomen, or elsewhere on the patient. The ultrasound transducer may be attached to the patient's body such that the ultrasonic transducer is aimed toward one or more major blood vessels, or another anatomical structure. For example, an ultrasound transducer that is attached to the suprasternal notch may be aimed toward the ascending aorta, the descending aorta or the aortic arch of the patient. An ultrasound transducer that is attached to the upper abdomen may be aimed toward the descending aorta of the patient. In some cases, the ultrasound transducer may have dimensions that are less than 3 centimeters. For example, a length or width of the ultrasound transducer may be in the range of 1 cm to 1.5 cm.

An adhesive patch may be provided to hold the ultrasound transducer to the patient's body. The adhesive patch may include a probe holder that includes a frame, receptacle, socket, or other structure for holding the ultrasound transducer. For example, one or both of the ultrasound transducer and the probe holder may include clips, latches, magnets, pins, or other structure that is configured to engage corresponding structure (e.g., tabs, loops, ferromagnetic plates, bores, sockets, or other corresponding structure) of the other.

The adhesive patch includes one or more adhesive surfaces. The adhesive surfaces are configured to adhere to the patient's skin when placed or pressed against the skin surface. For example, the adhesive surfaces may form an outer boundary of the adhesive patch, e.g., in the form of a circular, rectangular, or otherwise shaped ring. The size and shape of the adhesive surfaces may be configured to effectively hold the adhesive patch to a particular region of the patient's skin. For example, the size and shape may be configured to hold the adhesive patch to the patient's suprasternal notch or to the patient's upper abdomen.

Alternatively or in addition to an adhesive patch, the probe holder may be attached to the patient's body using suction, straps, clips, or otherwise.

The adhesive patch includes a structure for containing an acoustic coupling material between the ultrasound transducer and the patient's skin. For example, the acoustic coupling material may include an acoustic coupling gel, grease, or other material that may enable efficient propagation of ultrasound signals between the ultrasonic transducers and the skin surface. The structure for holding the acoustic coupling material may include walls to form a bath or chamber that may be fully or partially filled with the acoustic coupling material.

The system may be configured to operate the ultrasonic transducer elements to operate concurrently or alternately in B-mode and in Doppler mode. For example, Doppler and B-mode and measurements may be interleaved with instantaneous switching between Doppler and B-mode pulse sequences. During operation in B-mode, an ultrasound B-mode image of the interior of the patient may be acquired. The image may be expected to include an image of one or more sections of an internal object such as the patient's aorta. For example, when the ultrasound transducer is attached to the suprasternal notch, the image may include part of the ascending aorta or the aortic arch. When the ultrasound transducer is attached to the upper abdomen, the image may include part of the descending aorta.

One or more image processing techniques may be applied to the acquired image to automatically detect and identify one or more target sections. For example, automatic detection of the target section may be based on one or more of an expected size of the target section, a characteristic shape of the target section, a position of the target section relative to other identifiable anatomic features, or other detected or measured features. Various ultrasound imaging and display modes may be utilized, such as B-mode, motion mode (M-mode), color Doppler, spectral Doppler, or other modes.

For example, detection may be based on performing a template matching procedure. An acquired image may be compared to a bank of typical ultrasound images of the region that includes the target section. Correspondence of the acquired image with each image in the bank may be assessed by comparing the image correlation scores of the acquired image with different images in the image bank. Other techniques may be applied.

Upon identification in the image of the target section, one or more parameters of the target section may be derived from the image. For example, a diameter of the cross section of a target section of the aorta may be automatically measured from identified boundaries of the aorta. In some cases, at least an approximate orientation of the identified target section relative to the ultrasound transducer may be automatically determined, e.g., by comparison with images neighboring or other identified anatomical features, or by other characteristics (e.g., from analysis of blood flow within a target section of the aorta).

Continued operation in B-mode may be controlled such that the target section remains in subsequent acquired images. For example, an orientation of an imaged sector may be adjusted such that the target section remains at an approximately constant position within the acquired images.

When the ultrasonic transducer is operated in Doppler mode, the Doppler measurement ultrasound beam may be steered toward, focused on, or both the identified target section. For example, the ultrasound transducer may be operated to obtain a measurement of a velocity of the blood in an identified target section of a blood vessel such as the aorta. By alternating between operation of the ultrasound transducer in B-mode and operation in Doppler mode, the ultrasonic beam during operation in Doppler mode may be kept aimed at and focused on the target section. For example, the period of alternation may be sufficiently short such that typical anticipated body movements (e.g., breathing, voluntary movement of a limb, head, or other body part, or other relatively slow movements) do not significantly change the position of the ultrasound transducer relative to the target section. Alternatively or in addition, a sensor measurement may be used for gating the ultrasonic measurements in accordance with detected movements (e.g., heartbeat, breathing, or other cyclic motions).

For example, when the ultrasound transducer is operated in Doppler mode, ultrasound beam may be scanned over the identified target section. Thus, the velocity of the blood flow at different points on a cross section of the target section of the aorta may be measured. One or more of the measured blood flow velocity profile, measured dimensions (e.g., diameter or other dimension) of the target section, a measured heartbeat rate (e.g., measured using the ultrasound transducer or measured otherwise), or other measured quantities may be utilized to calculate a stroke volume, or one or more other hemodynamic parameters. In some cases, e.g., when the ultrasound transducer is placed at the suprasternal notch and the target section is the ascending aorta, the direction of the blood flow may be assumed to be approximately parallel to the direction of the ultrasound beam. For example, measurements may be limited to a plane (or spherical cap) that is approximately perpendicular to the ultrasound beam.

In some cases, e.g., when the ultrasound transducer is placed on the upper abdomen and the target section is the descending aorta, the measured blood flow profile may be utilized to calculate an angle between the direction of blood flow in the target section and the direction of the ultrasound beam. The calculated angle may be used in calculating the stroke volume.

A continuous ultrasonic monitoring system in accordance with an embodiment of the present invention may be advantageous over other techniques or devices for hemodynamic monitoring. A continuous ultrasonic monitoring system in accordance with an embodiment of the present invention enables continuous noninvasive hemodynamic monitoring. The continuous ultrasonic monitoring system may be prepared for operation and operated quickly and easily by a technician who lacks extensive medical training. Once the continuous ultrasonic monitoring system is prepared for use, the system may be left alone to continue monitoring, with no further attention or handling on the part of any personnel (or entail, at most, minimal adjustment).

For example, invasive hemodynamic monitors require insertion of a catheter into a blood vessel. Using an invasive monitor, requiring skill and time to insert the catheters and obtain the measurements, could entail delays that could lead to increased complications in treatment. Furthermore, the high cost per use of invasive hemodynamic monitors may limit the number of patients that may be monitored at the same time. Administering fluid treatment without hemodynamic monitoring, and thus without determining the responsiveness of a patient to treatment, could result in increased in morbidity, mortality, or a longer stay in a hospital.

Typical ultrasound systems may be utilized to estimate blood flow velocities by transmitting streams of high-frequency sound waves and analyzing the signals reflected from circulating red blood cells. Currently, most ultrasound Doppler techniques measure the component of blood velocity that is parallel to the direction of the beam. These one-dimensional measurements depend on the spatial angle between the transmitted beam and the direction of the flow. Development of vector Doppler methods that apply apodization may create a transverse modulation of the ultrasound beam, thus enabling the measurement of the flow velocity within an entire two-dimensional imaging plane. Extension of vector Doppler imaging to three dimensions entails using expensive two dimensional matrix transducers and high-end scanners. Current ultrasound imaging methodology requires manual handling, e.g., positioning and aiming, of the ultrasound probe. Thus, the use of ultrasound in fluid resuscitation management may be limited in a situation (e.g., an operating room or emergency room) where access to the patient is required from several directions, or where trained personnel are required for the performance of more urgent tasks.

FIG. 1 shows a block diagram of a system for continuous ultrasonic monitoring, in accordance an embodiment of the present invention.

Continuous ultrasonic monitoring system 10 is configured to monitor one or more hemodynamic parameters of a patient. Ultrasound transducer 12 of continuous ultrasonic monitoring system 10 is configured to be attached to a surface of the skin of the patient.

Ultrasound transducer 12 includes an array of ultrasonic transducer elements 14. The array may be linear, curved, or two dimensional. Each ultrasonic transducer element 14 may include a piezoelectric transducer, a capacitive micromachined ultrasonic transducer (CMUT), or another suitable ultrasonic transducer element.

For example, the array of ultrasonic transducer elements 14 may be controlled to function as a phased array to produce or receive a steerable ultrasound signal. For example, the signal may be in the form of a pulsed ultrasound signal (e.g., equivalent to a series of continuous waves having a particular spectrum of wavelengths and phases). Ultrasound transducer 12 may be configured to generate ultrasound signals that may be transmitted to, and whose reflections may be received from, points within ultrasound field of view 16 of ultrasound transducer 12. Ultrasound field of view 16 represents a substantially planar range, whose thickness is much smaller than its other dimensions.

Controller 20 is configured to control operation of ultrasound transducer 12 and of associated electronics to as to obtain a desired measured result. For example, the measured result may include a B-mode image of ultrasound that is reflected from various structures within a patient's body, or a Doppler mode measurement of a velocity of an object or collection of objects (e.g., blood cells) within the patient's body.

Controller 20 may include a standalone unit that includes processing capability and is dedicated to operation of continuous ultrasonic monitoring system 10. Alternatively or in addition, controller 20 may include a software module, circuit board, or other software or hardware components that are incorporated within, connected to, or otherwise hosted by a general purpose computer.

A processor of controller 20 may be configured to operate in accordance with programmed instructions. For example, the programmed instructions may be stored in a memory or data storage device with which the processor is configured to communicate.

One or more of transmit beam former 22, receive beam former 24, and a digital processing unit may include a separate or distinguishable hardware component or circuitry within controller 20, a software module of programmed instructions for operation of a processor or processing unit of controller 20, or may represent a functionality of controller 20.

Transmit beam former 22 is configured to individually control transmission by each ultrasonic transducer element 14 so as to produce an ultrasonic beam with particular characteristics. The relative phases, amplitudes, and pulse shapes of ultrasound signals that are produced by each ultrasonic transducer element 14 may be controlled to form an ultrasonic beam having particular characteristics. For example, the beam may be aimed in a selectable direction within ultrasound field of view 16, or to modify ultrasound field of view 16 (e.g., rotate ultrasound field of view 16 or change the distance to the near and far boundaries of ultrasound field of view 16). Alternatively or in addition, the relative phases may be controlled to form a beam that is focused at a selectable distance from ultrasonic transducer elements 14 within ultrasound field of view 16. Ultrasonic transducer elements 14 may be controlled to form plane waves.

The transmitted signal may be reflected back toward ultrasonic transducer elements 14. For example, the signal may be reflected from blood cells in the aorta or another blood vessel, from walls of the aorta or another blood vessel, or from another structure, surface, or interface within the patient's body. Ultrasonic transducer elements 14 may detect the reflected signal.

Receive beam former 24 may be operated to receive signals from a selectable direction within ultrasound field of view 16. For example, receive beam former 24 may control synchronization of the signals that are received by each ultrasonic transducer element 14 so as to detect (e.g., reflected) ultrasound signals that originate from a selectable direction relative to ultrasound transducer 12. Similarly, receive beam former 24 may control synchronization of the signals that are received by each ultrasonic transducer element 14 so as to detect ultrasound signals that originate from a selectable distance from ultrasound transducer 12.

The received signals may be processed by signal processing unit 28. Signal processing unit 28 may perform one or more functions for extracting a desired measurement from the received signal.

For example, signal processing unit 28 may be configured to distinguish a received reflected ultrasound pulse from a carrier wave (e.g., demodulation) or background noise (e.g. filtering).

Signal processing unit 28 may be configured to determine an intensity or amplitude ("brightness") of an ultrasound pulse that is received at each point within ultrasound field of view 16. Thus, signal processing unit 28 may produce a B-mode image of structure within ultrasound field of view 16.

Signal processing unit 28 may be configured to operate in Doppler mode to calculate the phase shifts of consecutive ultrasound pulses that are reflected from a point or region within ultrasound field of view 16. These phase shifts may be analyzed to yield a component of velocity of the structure that reflected the pulses toward or away from ultrasound transducer 12. For example, if the structure includes blood cells, the measurement may yield a velocity of a component of the blood flow toward or away from ultrasound transducer 12.

A processing capability of controller 20 may analyze results from measurements using ultrasound transducer 12 to yield one or more hemodynamic parameters. For example, results of B-mode operation and Doppler mode operation may be utilized to calculate a stroke volume, or another hemodynamic parameter.

A user of continuous ultrasonic monitoring system 10 may operate controller 20 via user interface 30. For example, user interface 30 may include one or more screen controls or input devices (e.g., switches, pushbuttons, levers, dials, knobs, touch screens, pointing devices, keyboards, keypads, or other input devices) that enable a user to input one or more instructions to controller 20. For example, instructions may include an instruction to begin or stop operation, operating parameters, patient information, or other instructions.

Results of operation of continuous ultrasonic monitoring system 10 may be displayed on monitor 32. For example, alphanumeric characters may be displayed on monitor 32 to indicate the value of one or more hemodynamic parameters, such as stroke volume, heartbeat rate, or other hemodynamic parameters. For Monitor 32 may be operated to display warnings or notifications to a user, results of analysis (e.g., a stroke volume or other hemodynamic parameter), patient information, or other information.

Monitor 32 may display an ultrasound image 34. Ultrasound image 34 may include an image or one or more anatomical structures 36 (e.g., the aortic arch, descending aorta, heart, or other structure of interest). For example, ultrasound image 34 may include a B-mode image of anatomical features within ultrasound field of view 16. In some cases, a B-mode image may be modified to display additional information. For example, parts of ultrasound image may be color coded or otherwise modified to display velocity results of Doppler mode measurements, e.g., within images of the aorta, or where Doppler mode measurements were made.

In some cases, continuous ultrasonic monitoring system 10 may include, or may be configured to communicate with, other types of sensors. Such additional sensor may include electrocardiogram electrodes, a pulse oximeter, a respiration monitor, a blood pressure monitor, or another type of sensor. In some cases, one or more sensors, or one or more electrodes of a sensor, may be incorporated into ultrasound measurement assembly 40 (e.g., in adhesive outer rim 42 or elsewhere). Results of such other sensors may be utilized in calculating values of additional hemodynamic parameters. Alternatively or in addition, results of such sensor measurements may be utilized to correct or adjust the ultrasound measurements (e.g., by enabling the filtering of noise, or otherwise).

Figure 2A:
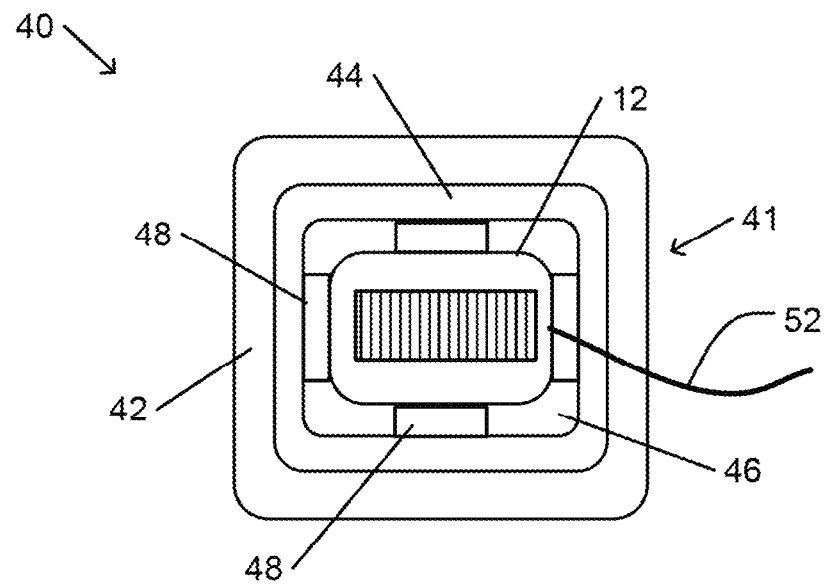
FIG. 2A schematically illustrates an ultrasound measurement unit of the system shown in FIG. 1.
Figure 2B:
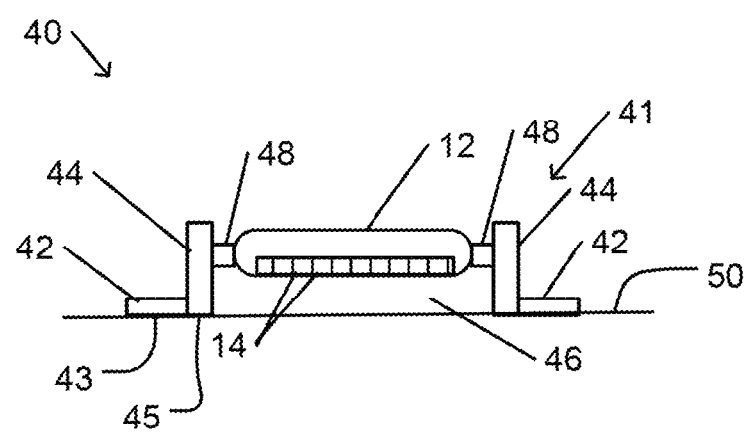
FIG. 2B is a schematic sectional view of the ultrasound measurement unit shown in FIG. 2A.

FIG. 2A schematically illustrates an ultrasound measurement unit of the system shown in FIG. 1. For example, FIG. 2A may schematically represent the ultrasound measurement unit as viewed from the bottom (viewing the side that is configured for attachment to the skin surface). FIG. 2B is a schematic sectional view of the ultrasound measurement unit shown in FIG. 2A.

Ultrasound measurement assembly 40 includes ultrasound transducer 12 mounted on ultrasound transducer holder 41. Ultrasound transducer holder 41 is configured to hold ultrasound transducer 12 such that ultrasonic waves may pass efficiently between ultrasonic transducer elements 14 and skin surface 50 (and tissue below skin surface 50). Part or all of ultrasound transducer holder 41 may be designed to be disposable after a single use. For example, ultrasound transducer holder 41 may be in the form of a patch that may be caused to adhere to the patient's skin. In some cases, one or more components of ultrasound transducer holder 41 may be designed to be cleanable, sterilizable, or otherwise configured to enable single or multiple reuse of those components.

Ultrasound transducer holder 41 includes one or more adhesive surfaces that are coated with a material that is designed to adhere to skin surface 50. The adhesive material may include a standard medical or surgical adhesive, or another material that includes one or more properties that make it suitable for use on skin, such as adherence to skin, being hypoallergenic, being removable from skin without discomfort or without leaving excessive residue, or other properties.

Alternatively or in addition to adhesive surfaces, ultrasound transducer holder 41 may include other structure for holding ultrasound transducer holder 41 to skin surface 50. For example, ultrasound transducer holder 41 may include one or more suction cups, vacuum ports, straps, clamps, or other components for holding ultrasound transducer holder 41 to skin surface 50.

The adhesive surfaces may be arranged so as to avoid interfering with the transmission of ultrasound waves from or to ultrasonic transducer elements 14. For example, the adhesive strips may be arranged in the form of adhesive outer rim 42 that partially or fully surrounds other components at the periphery of ultrasound transducer holder 41. Adhesive outer rim 42 may have an approximately square or rectangular form (or a rounded square or rectangular form), as shown, or may have another form (e.g., circular, oval, polygonal, or another form). Adhesive outer rim 42 may have a closed form as shown, or may include one or more gaps. In some cases, additional strips or pieces of adhesive may be located interior to adhesive outer rim 42.

For example, prior to use, adhesive surface 43 of adhesive outer rim 42 may be covered with a removable layer of paper, plastic, or another type of material. After removal of the cover, adhesive surface 43 may be placed at a user-selected location on skin surface 50. Application of pressure to the side of adhesive outer rim 42 opposite adhesive surface 43 may cause adhesive surface 43 to adhere to skin surface 50.

Ultrasound transducer holder 41 includes coupling material retaining structure 44. Coupling material retaining structure 44 may include walls or similar structure that is configured to retain an ultrasound coupling material (e.g., typically in the form of a gel or grease) within coupling material retaining structure 44. For example, walls of coupling material retaining structure 44 may be made of plastic, or another material, that is impermeable to the ultrasound coupling material. Walls of coupling material retaining structure 44 may be held against skin surface 50, e.g., when adhesive surface 43 of adhesive outer rim 42 adheres to skin surface 50. When held against skin surface 50, the walls of coupling material retaining structure 44 and skin surface 50 form a container or tub with interior space 46. Interior space 46 of coupling material retaining structure 44 may be filled with the ultrasound coupling material. Thus the coupling material may be retained in interior space 46 to fill the volume between ultrasonic transducer elements 14 of ultrasound transducer 12 and skin surface 50.

In some cases, end surface 45 of the walls of coupling material retaining structure 44 may be designed to form a seal with skin surface 50. For example, end surface 45 may include a flexible material (e.g., rubber, silicone, or another flexible plastic or material) that functions as a gasket when end surface 45 is held against skin surface 50. Thus, when end surface 45 of coupling material retaining structure 44 is held against skin surface 45, the flexible material may prevent seepage or the ultrasound coupling material may be configured to retain the ultrasound coup between coupling material retaining structure 44 and skin surface 50. (Prevention of such seepage may be desirable, in addition to prevention of loss of the ultrasound coupling material, in order to prevent interference of the ultrasound coupling material with adhesion of adhesive surface 43 to skin surface 50.)

The walls of coupling material retaining structure 44, or other structure of ultrasound transducer holder 41, may include holding structure 48 for holding ultrasound transducer 12. For example, holding structure 48 may include one or more clips, tabs, slots, pins, or other structure that is configured to engage corresponding structure of ultrasound transducer 12. For example, a clip or pin of holding structure 48 may be elastically bendable, spring loaded, or otherwise configured such that when ultrasound transducer 12 is pushed into a socket or other part of ultrasound transducer holder 41, the clip or pin is extended to engage a corresponding slot, socket, or hole on ultrasound transducer 12.

Holding structure 48 may be configured such that when ultrasound transducer 12 is held by holding structure 48, and when coupling material retaining structure 44 is filled with ultrasound coupling material, ultrasonic transducer elements 14 of ultrasound transducer 12 is submerged in the ultrasound coupling material. Furthermore, holding structure 48 may be configured so as to aim ultrasonic transducer elements 14 toward structure of interest (e.g., a section of the aorta or another structure) below skin surface 50 (e.g., when ultrasound transducer holder 41 is placed at one or more predetermined positions on skin surface 50, e.g., at the suprasternal notch or on the upper abdomen). In some cases, part of ultrasound transducer holder 41 (e.g., adhesive outer rim 42, or another part) may be provided with markings to facilitate placement of ultrasound transducer holder 41 at one or more standard positions on skin surface 50. Thus, ultrasonic waves may be transmitted efficiently and effectively between ultrasonic transducer elements 14 and structure of interest (e.g., the aortic arch or the descending aorta) beneath skin surface 50 of a patient.

Ultrasound transducer 12 may be connected to transmit beam former 22, receive beam former 24, controller 20, or other components of continuous ultrasonic monitoring system 10 via cable 52. Alternatively of in addition, ultrasound transducer 12 may be connected to other components of continuous ultrasonic monitoring system 10 via a wireless connection.

Continuous ultrasonic monitoring system 10 may be configured to execute a method for continuous ultrasonic monitoring, in accordance an embodiment of the present invention.

Figure 3A:
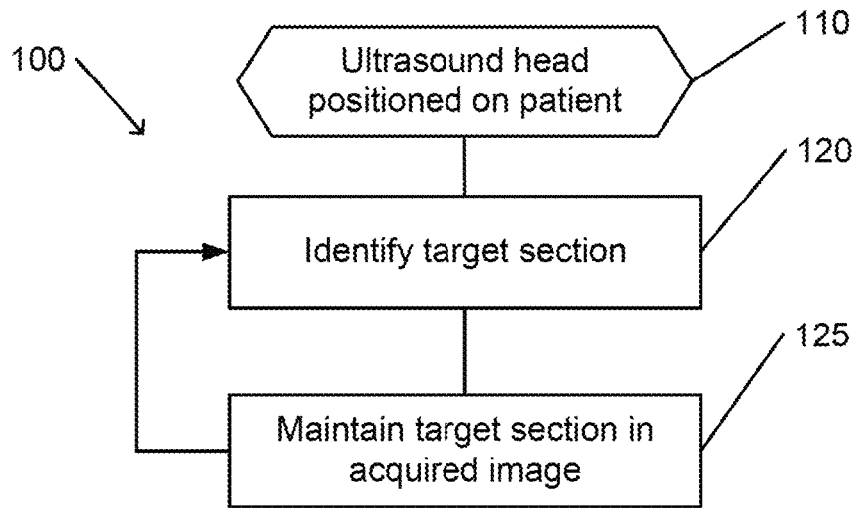
FIG. 3A is a flowchart depicting a method for continuous ultrasonic monitoring, in accordance with an embodiment of the present invention.

FIG. 3A is a flowchart depicting a method for continuous ultrasonic monitoring, in accordance with an embodiment of the present invention.

It should be understood with respect to any flowchart referenced herein that the division of the illustrated method into discrete operations represented by blocks of the flowchart has been selected for convenience and clarity only. Alternative division of the illustrated method into discrete operations is possible with equivalent results. Such alternative division of the illustrated method into discrete operations should be understood as representing other embodiments of the illustrated method.

Similarly, it should be understood that, unless indicated otherwise, the illustrated order of execution of the operations represented by blocks of any flowchart referenced herein has been selected for convenience and clarity only. Operations of the illustrated method may be executed in an alternative order, or concurrently, with equivalent results. Such reordering of operations of the illustrated method should be understood as representing other embodiments of the illustrated method.

Continuous ultrasonic monitoring method 100 may be executed by a processor of controller 20 of continuous ultrasonic monitoring system 10. Execution of continuous ultrasonic monitoring method 100 may be initiated by a user or operator of continuous ultrasonic monitoring system 10.

Controller 20 may be instructed to initiate execution of continuous ultrasonic monitoring method 100 after ultrasound measurement assembly 40, with ultrasound transducer holder 41 and ultrasound transducer 12, has been positioned on, and attached to, skin surface 50 of a patient (block 110). Ultrasonic transducer elements 14 of ultrasound transducer 12 may be aimed in the general direction of a target section of a suitable anatomical structure (e.g., an anatomical structure with features that are identifiable in an ultrasound image).

For example, continuous ultrasonic monitoring system 10 may be operated in B-mode to obtain one or more images of a sector of the interior of the patient. The acquired images may be analyzed to identify the location of the target section relative to ultrasound transducer 12 (block 120).

Continuous ultrasonic monitoring system 10 may be operated to repeatedly steer and focus the ultrasound beam to maintain the target section within an acquired ultrasound image (block 125). For example, ultrasound field of view 16 may be moved such that an image of the target section remains within a subsequently acquired image, or at an approximately constant position within the acquired image.

The operations of identifying the target section (e.g., in an acquired image) and maintaining the image of the target section within acquired images may be repeated at frequent intervals (repeating continuously the operations of blocks 120 and 125). Thus, the target section may be continuously monitored using ultrasound measurements.

In particular, continuous ultrasonic monitoring system 10 may be configured to execute a method for ultrasonic continuous hemodynamic monitoring, in accordance with an embodiment of the present invention.

Figure 3B:
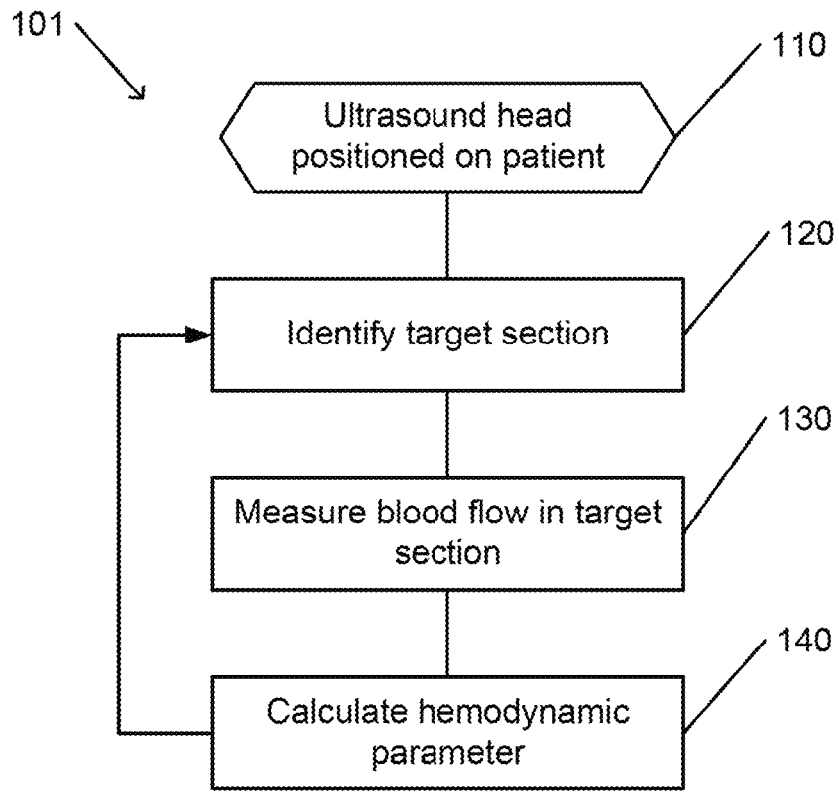
FIG. 3B is a flowchart depicting a method for ultrasonic continuous hemodynamic monitoring, in accordance with an embodiment of the present invention.

FIG. 3B is a flowchart depicting a method for ultrasonic continuous hemodynamic monitoring, in accordance with an embodiment of the present invention.

Continuous hemodynamic monitoring method 101 may be executed by a processor of controller 20 of continuous ultrasonic monitoring system 10. Execution of continuous hemodynamic monitoring method 101 may be initiated by a user or operator of continuous hemodynamic ultrasonic monitoring system 10.

Controller 20 may be instructed to initiate execution of continuous hemodynamic monitoring method 101 after ultrasound measurement assembly 40, with ultrasound transducer holder 41 and ultrasound transducer 12, has been positioned on, and attached to, skin surface 50 of a patient (block 110). For example, ultrasound transducer holder 41 may be attached to the suprasternal notch, upper abdomen, or another suitable location on the patient. Ultrasonic transducer elements 14 of ultrasound transducer 12 may be aimed in the general direction of a target section of the aorta, or at another suitable anatomical structure.

Continuous ultrasonic monitoring system 10 may be operated in B-mode to obtain one or more images of the interior of the patient. The acquired images may be analyzed to identify the location of the target section relative to ultrasound transducer 12 (block 120).

Continuous ultrasonic monitoring system 10 may be operated in Doppler mode to measure the velocity of the blood flow at various parts of the target section (block 130). For example, the direction and focal distance of the transmitted and received ultrasound beam may be directed to various points of the target section, as determined from analysis of the B-mode images.

One or more hemodynamic parameters, such as stroke volume, may be calculated on the basis of the measured blood flow and geometry of the target section (block 140). For example, flow rates may be summed over a cross section of the target section of the aorta and integrated over time to yield at least an initial estimate of the stroke volume. Adjustments and corrections to the calculation may be required.

In some cases, measurements in an approximately straight section of the target section (e.g., the descending aorta) may be analyzed to yield an angle of the target section relative to the ultrasound beam. Knowledge of the angle may enable derivation of an actual (total or absolute) blood velocity from an ultrasound measurement of a component of the velocity that is parallel to the beam direction.

Figure 4:
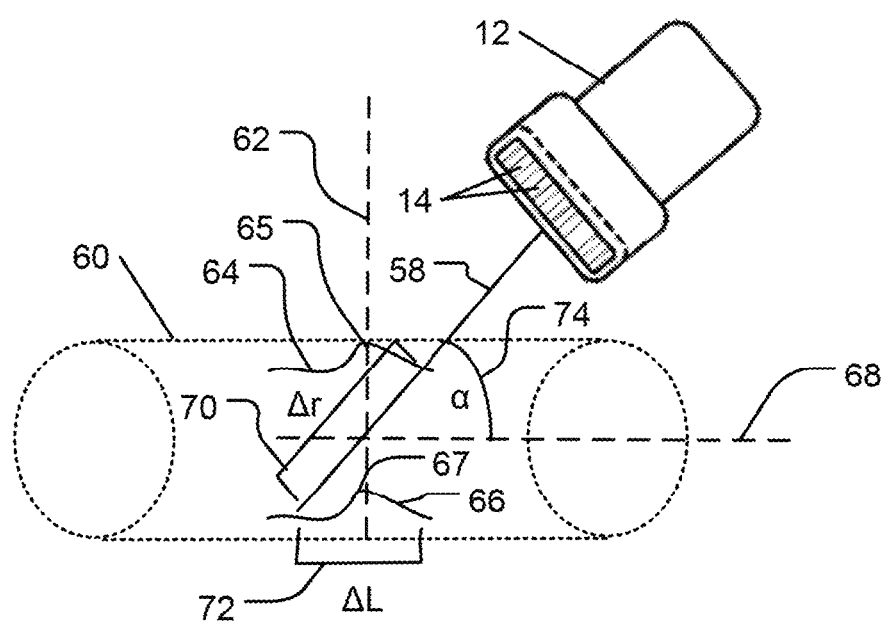
FIG. 4 illustrates determination of a flow direction from a measurement made with the ultrasound measurement unit shown in FIG. 2A.

FIG. 4 illustrates determination of a flow direction from a measurement made with the ultrasound measurement unit shown in FIG. 2A.

In this case, value α of angle 74 may be calculated. Angle 74 is the angle between beam direction 58 and vessel axis 68 of target section 60 (e.g., of a blood vessel such as the descending aorta). Measurements of velocity profiles 64 and 66 may be made at two points that are equidistant from vessel axis 68 (and assumed to have the same actually flow velocity, assuming laminar flow of the blood in target section 60, which implies an axially symmetric velocity profile). Velocity profile 64 includes peak 65, and velocity profile 66 includes peak 67 which is assumed to correspond to peak 65 with an additional time delay due to the increased distance from ultrasonic transducer elements 14.

Measured velocity x(t) as a function of time t may be written for velocity profile 64 as $x(t)=s(t)+n_1(t)$, and measured velocity y(t) for velocity profile 66 at a more distant point may be written as $y(t)=s(t+d)+n_2(t)$, where s(t) is the ultrasound signal, n(t) is noise that is added to each signal, and d is a time delay due to the distance between the measurement points.

The cross correlation between the two signals $R_{xy}(\tau)=R_{ss}(\tau+d)$, the correlation between the signal and the signal after time delay d. Since the cross correlation $R_{xy}(\tau)$ reaches its maximum value at $\tau=-d$, the time delay d may be derived from the cross correlation.

During time delay d, the blood moving at (actual unknown) velocity V travels a distance 72 with value $\Delta L=d\cdot V$.

The component of velocity V that is measured along beam direction 58 may be written as $v=V\cos(\alpha)$. Distance component 70, measured to be $\Delta r$, between the points of measurement of velocity profiles 64 and 66 is $\Delta r=\Delta L/\cos(\alpha)$.

Therefore, $\Delta r=\Delta L/\cos(\alpha)=d\cdot V/\cos(\alpha)=d\cdot v/\cos^2(\alpha)$.

Therefore, value $\alpha$ of angle 74 may be derived from measured values (for the assumed symmetry of the velocity profile):

$$\alpha=\arccos(\sqrt{d\cdot v/\Delta r})$$

In other cases, e.g., where the target section includes the aortic arch, it may be possible to perform measurements on a part of the target section whose cross section is close to perpendicular to the beam direction.

The operations of alternating B-mode image acquisition and Doppler mode velocity measurements may be repeated at frequent intervals. During each interval, the hemodynamic parameters may be calculated (repeating continuously the operations of blocks 120 to 140).

Thus, the hemodynamic parameters may be continuously monitored using ultrasound measurements.

For example, hemodynamic parameters may be monitored both prior to and after application of fluid resuscitation or of fluid infusion to a patient. In this way, a physician or other healthcare administrator may be able to treat a patient with reduced risk of improper treatment.

In accordance with an embodiment of the present invention, an ultrasound measurement assembly may include a built-in layer of ultrasound coupling material. For example, the ultrasound measurement assembly may include a capsule that is filled with an ultrasound gel, a pad that is impregnated with an ultrasound gel or grease, or another ultrasound coupling structure.

A holding structure of the ultrasound measurement assembly for holding an ultrasound transducer may enable manual or actuated movement of the ultrasound transducer. The movement may include rotation, translation, or both. For example, the ultrasound transducer may be enclosed in an enclosure that includes a mechanism for altering an orientation of the ultrasound transducer about one or more axes, or for translating the ultrasound transducer along one or more axes. For example, linear translation may include pressing the ultrasound transducer toward the skin surface so as to improve the imaging of structure inside the body.

An ultrasound transducer, and, in some cases, a motorized or actuated orientation adjusting mechanism, translation mechanism, or both, may be connected to an external controller by a wireless connection. For example, an enclosure of the ultrasound transducer may include one or more components that enable wireless communication with an external device.

Figure 5A:
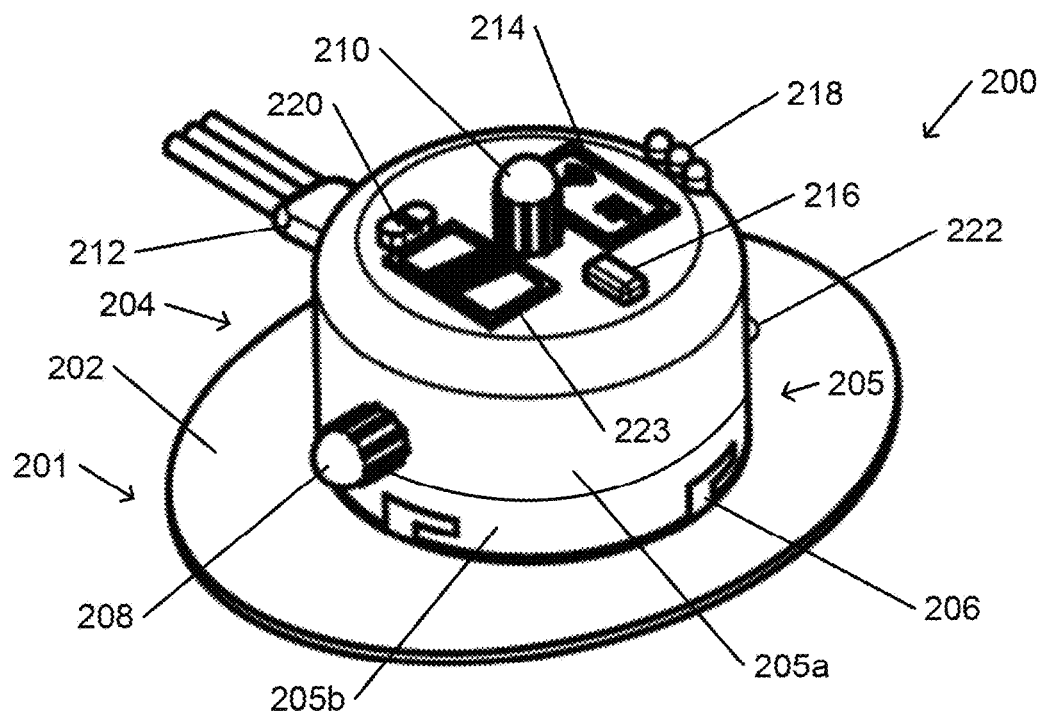
FIG. 5A schematically illustrates an ultrasound measurement assembly with a mechanically orientable transducer, in accordance with an embodiment of the present invention.
Figure 5B:
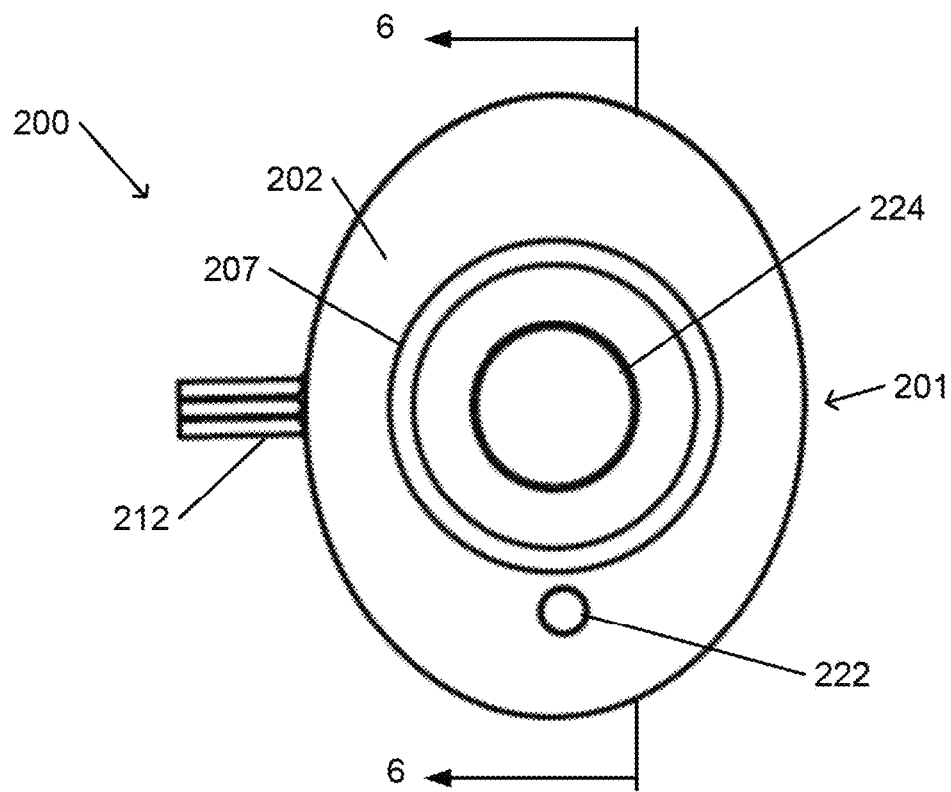
FIG. 5B schematically illustrates a bottom surface of the ultrasound measurement assembly shown in FIG. 5A.
Figure 5C:
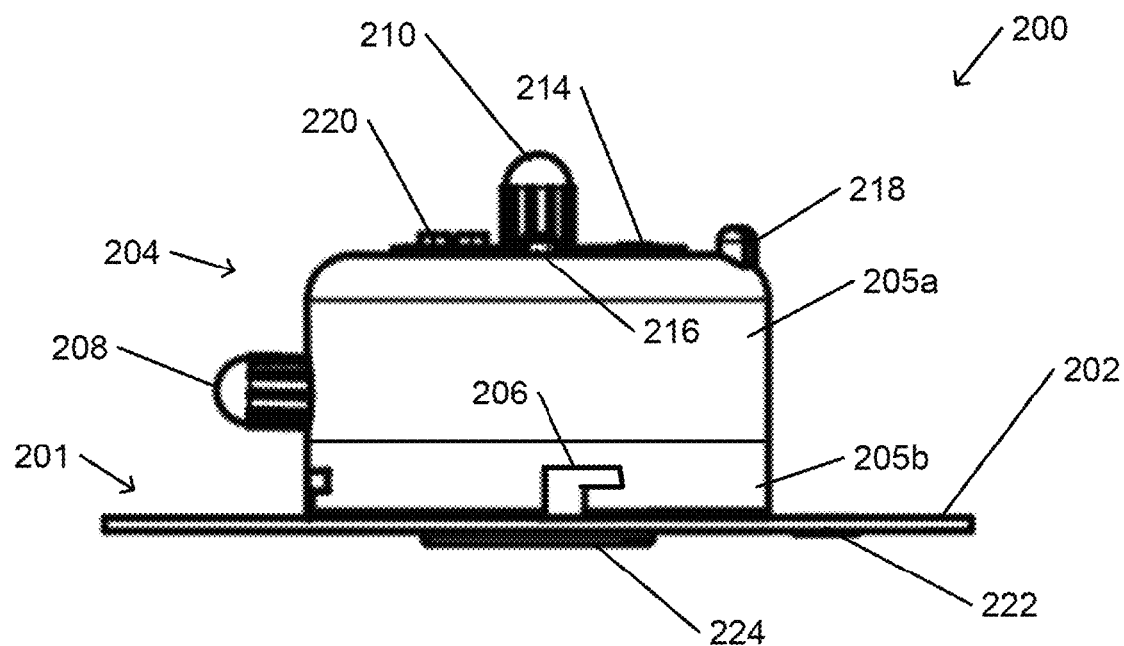
FIG. 5C schematically illustrates a side view of the ultrasound measurement assembly shown in FIG. 5A.

FIG. 5A schematically illustrates an ultrasound measurement assembly with a mechanically movable transducer, in accordance with an embodiment of the present invention. FIG. 5B schematically illustrates a bottom surface of the ultrasound measurement assembly shown in FIG. 5A. FIG. 5C schematically illustrates a side view of the ultrasound measurement assembly shown in FIG. 5A.

Ultrasound measurement device 204 of ultrasound measurement assembly 200 includes an ultrasound transducer 230 (shown in FIG. 6) and components to enable movement or aiming of, control of, and communication with ultrasound transducer 230. Ultrasound measurement device 204 may be enclosed in enclosure 205. For example, enclosure 205 may be constructed of a suitable plastic or metal material.

Fixed enclosure section 205b of enclosure 205 may be attached to enclosure seat 207 of adhesive patch 201 by attachment structure 206 of adhesive patch 201. For example, enclosure seat 207 may include a rigid section, socket, or rack structure that is shaped (e.g., molded, machined, or otherwise shaped) to receive fixed enclosure section 205b. Enclosure seat 207 may be molded from plastic or otherwise formed. Attachment structure 206 may include clips, pins, latches, or another attachment structure. Enclosure seat 207 and attachment structure 206 may be configured to hold enclosure 205 and ultrasound measurement device 204 at a fixed position and orientation relative to adhesive patch 201.

Adhesive patch 201 may be configured to hold ultrasound measurement assembly 200 to a skin surface. For example, an adhesive section 202 of adhesive patch 201 may include an adhesive surface that may be exposed by removing (e.g., peeling off) a protective cover layer (e.g., made of a flexible plastic sheet). The exposed adhesive may be placed on or pressed onto a skin surface in order to hold ultrasound measurement assembly 200 to the skin surface.

Adhesive patch 201 may be disposable, including only relatively inexpensively made standard components. All reusable (e.g., electronic and relatively expensive) components of ultrasound measurement assembly 200 may be included in ultrasound measurement device 204. Direct contact of ultrasound measurement device 204 with the skin surface may thus prevented by adhesive patch 201. Since ultrasound measurement device 204 does not directly contact the skin of a patient, ultrasound measurement device 204 may be reusable with different patients after light cleaning, without requiring sterilization. In some cases, ultrasound measurement device 204 may be constructed of inexpensive hardware components. For example, ultrasound transducer 230 may include a capacitive micro-machined ultrasonic transducer. In such a case, ultrasound measurement device 204 may also be disposable, such that all of ultrasound measurement assembly 200 may be disposable.

Adhesive patch 201 may include ultrasound coupler 224. For example, ultrasound coupler 224 may include a capsule that is filled with, or made of, an ultrasound gel or grease. Thus, ultrasound measurement assembly 200 may be used to make subcutaneous ultrasound measurements without application of an ultrasound gel or grease. Therefore, preparation of ultrasound measurement assembly 200 for use, and reuse of ultrasound measurement device 204 and enclosure 205, may be expedited by eliminating any requirement for extensive cleaning to remove an externally applied ultrasound coupling medium.

Adhesive patch 201 may include an electrode 222. For example, electrode 222 may enable connection of adhesive patch 201 to an electrocardiography device or similar device configured to measure electric or electromagnetic signals. For example, connection to an electrocardiography device may enable ultrasound measurements that are synchronized with a patient's heartbeat or cardiac cycle. The electrocardiography signal may be processed by a controller that is associated with ultrasound measurement assembly 200 (e.g., device controller 240, controller 20 of continuous ultrasonic monitoring system 10, or another controller).

Ultrasound measurement device 204 is configured to enable manual rotation or aiming of an ultrasound transducer. For example, axial knob 210 may be rotated by a user of ultrasound measurement assembly 200 to axially rotate rotatable enclosure section 205a, including an enclosed ultrasound transducer, relative to fixed enclosure section 205b. Tilt knob 208 may be rotated by the user to tilt the enclosed ultrasound transducer relative to fixed enclosure section 205b and adhesive patch 201, and thus relative to the skin surface. In this manner, two-axis aiming of ultrasound transducer 230 may be enabled.

In some cases, axial knob 210 may be configured to be pushed inward. The inward pushing on axial knob 210 may press ultrasound transducer 230 toward adhesive patch 201 and the skin surface. For example, pressing ultrasound transducer 230 toward the skin surface may enable improved image by ultrasound transducer 230 of internal structures of the patient's body.

Ultrasound measurement device 204 may be configured to be connected by wire connector 212 to an external source of electric power, to a controller, or to other devices or components, e.g., of a continuous hemodynamic ultrasonic monitoring system 10 or other system. Wire connector 212 may enable connecting ultrasound measurement device 204 to a fixed or portable external computer, to an external display or control unit, or to another type of device.

Ultrasound measurement device 204 may be configured to communicate wirelessly with one or more external devices (e.g., another ultrasound measurement device 204), via wireless communication device 214. For example, wireless communication device 214 may include a radiofrequency antenna, as shown, or another type of wireless communication device. The wireless connection may include a radiofrequency identification (RFID) patch, a barcode, or other structure to enable remote or automatic identification of a particular ultrasound measurement device 204. For example, such identification may be used to ensure that an ultrasound measurement device 204 is compatible with a particular ultrasound transducer 230 or adhesive patch 201, or to provide specific identification for each ultrasound measurement assembly 200 that is placed on a patient.

Ultrasound measurement device 204 may include one or more sensors 216 to sense one or more conditions. For example, a sensor 216 may include one or more motion and/or position sensors, such as accelerometers or proximity sensors (e.g., capacitive, potentiometric, or magnetic sensors), in order to ascertain the position or movement of the patch either relative to the patient body, with respect to other objects or devices (e.g., another ultrasound measurement assembly 200, a surgical or other tool, or another object or device) or in absolute coordinates. For example, the sensors may be utilized to predict and correct an ultrasound measurement based on motion or position, or to provide additional clinical information regarding patient motion, such as due to breathing or other motion.

Ultrasound measurement device 204 may be configured to enable direct operation of monitoring by a user. For example, ultrasound measurement device 204 may include one or more user-operable controls 220 (e.g., pushbuttons or other controls, e.g., to select between modes of operation or operation parameters). Ultrasound measurement device 204 may include indicator lights 218 (e.g., light emitting diodes or other types of indicators), a display 223 (e.g., a liquid crystal display), or other components or structure to enable monitoring by a user (e.g., to indicate a mode of operation, status, warning, or other indication).

Figure 6:
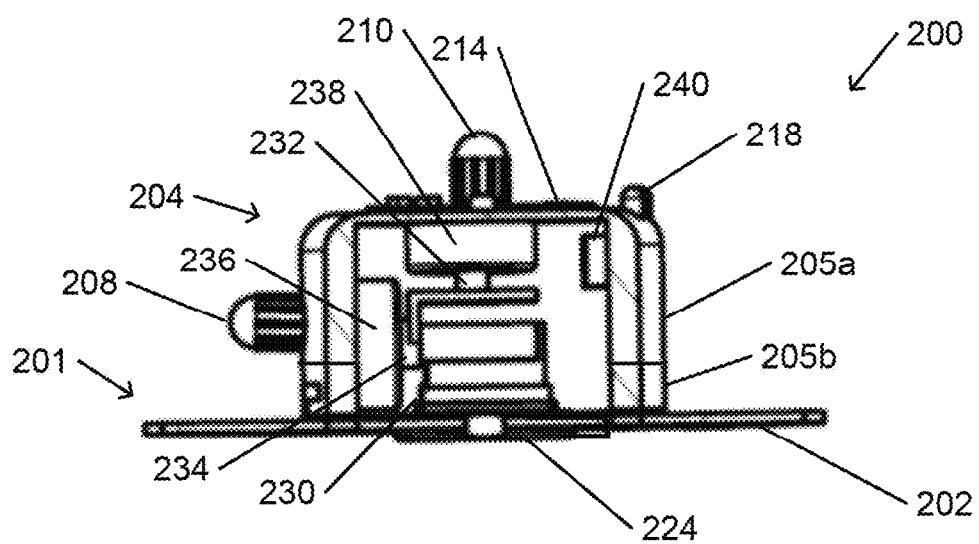
FIG. 6 schematically illustrates a sectional view of the of the ultrasound measurement assembly shown in FIG. 5C.

FIG. 6 schematically illustrates a sectional view of the of the ultrasound measurement assembly shown in FIG. 5C.

Ultrasound transducer 230 is mounted to tilt axis 234. Tilt axis 234 together with ultrasound transducer 230 may be tilted by manual rotation of tilt knob 208. Alternatively or in addition, ultrasound transducer 230 may be tilted about tilt axis 234 by operation of tilt actuator 236. For example, tilt actuator 236 may be operated by a user via wired or wireless communication with device controller 240. In some cases, an ultrasound measurement device may include only one of tilt knob 208 (for manual operation only) or tilt actuator 236 (for motorized or actuated operation only). In some cases, an ultrasound measurement device may include additional motors or actuators, or manual operation controls.

Tilt axis 234, tilt knob 208, and ultrasound transducer 230, together with rotatable enclosure section 205a and tilt actuator 236, are rotatable about axial rotation axis 232. For example, axial rotation axis 232 may be rotated by manual rotation of axial knob 210. Alternatively or in addition, axial rotation axis 232 and ultrasound transducer 230 may be axially rotated by operation of axial actuator 238. For example, axial actuator 238 may be operated by a user via wired or wireless communication with device controller 240. In some cases, an ultrasound measurement device may include only one of axial knob 210 (for manual operation only) or axial actuator 238 (for motorized operation only).

Device controller 240 may control one or more of operation of ultrasound transducer 230, axial actuator 238, tilt actuator 236, indicator lights 218, display 223, or another component of ultrasound measurement device 204. Device controller 240 may operate one or more sensors 216 and control operation of one or more components in accordance with a quantity that is sensed by a sensor 216. Device controller 240 may include circuitry, or one or more processors. Device controller may include a battery or other internal power supply (e.g., an energy producing mechanism or wireless charging mechanism).

Thus, an orientation of ultrasound transducer 230 may be mechanically adjustable along one or two orthogonal axes by manual operation of one or both of axial knob 210 and tilt knob 208. Alternatively or in addition to operation of knobs, an orientation of ultrasound transducer 230 may be mechanically adjusted by operation of one or more levers, dials, and knobs.

An orientation of ultrasound transducer 230 may be remotely, automatically, or otherwise electrically controlled by operation of one or both of axial actuator 238 and tilt actuator 236. Axial actuator 238 or tilt actuator 236 may include a direct current motor or alternating current motor that includes a geared motor, stepper motor, servomotor, actuator, another type of motor, or any combination of the above. Alternatively or in addition, an orientation adjusting mechanism may include one or more magnets, whose orientation may be controlled by a magnetic or electromagnetic field.

In some cases, axial actuator 238 (or another axially oriented linear actuator) may be configured to linearly translate ultrasound transducer 230 along, or parallel to, axial rotation axis 232. For example, linear translation of ultrasound transducer 230 by axial actuator 238 may press ultrasound transducer 230 toward adhesive patch 201 and the skin surface. For example, pressing ultrasound transducer 230 toward the skin surface may enable improved image by ultrasound transducer 230 of internal structures of the patient's body.

A motorized, hydraulic, or other remotely or electrically controllable orientation adjusting mechanism, e.g., that includes tilt actuator 236, axial actuator 238, both, or additional or alternative controllable mechanisms, may be operated to mechanically scan ultrasound transducer 230 over a range of orientations, or to mechanically translate ultrasound transducer 230 in one or more directions. For example, a scanning mechanism may enable scanning with one or more additional degrees of freedom (e.g., up to six degrees of freedom, e.g., by incorporating a Stewart platform mechanism, or otherwise). These degrees of freedom may include, or may be in addition to, the degrees of freedom that are attainable by electronically steering and focusing the ultrasound beam using phased array capabilities of ultrasound transducer 230. The scanning mechanisms may be automatically controlled by a scanner (e.g., incorporated into or communicating with device controller 240, controller 20 of continuous ultrasonic monitoring system 10, or another controller) to continuously modify the orientation of ultrasound transducer 230 to track a target object inside the body, such as an organ, blood vessel, surgical instrument, robot, or another object that is inside the body or that was inserted into the body.

For example, automatic tracking may include acquiring a sequence of ultrasound images, and processing the images to detecting a target object in the images. The scanner may measure the motion (e.g., speed, acceleration, curvature, or other parameter of the motion) of the object in each acquired frame of the ultrasound scan, and control the orientation of ultrasound transducer 230 so as to accommodate the measured motion.

In some cases, ultrasound measurement assembly 200 or ultrasound measurement device 204 may include a plurality of ultrasound transducers. An ultrasound transducer 230 may include a one- or two-dimensional array of ultrasonic transducer elements 14.

In some cases, an adhesive patch 201 or ultrasound measurement device 204 may be configured to hold and orient a standard commercially available ultrasound probe and handle. In this case, adhesive patch 201 may enable affixing the probe to a body to enable provide automatically adjustable, hands-free and stable operation.

Ultrasound measurement assembly 200 may be utilized to automatically monitor blood flow in a selected blood vessel inside a patient's body. For example, the blood vessel may be automatically detected in an ultrasound image by applying image processing techniques. Device controller 240 (or an external controller, such as controller 20, which is in communication with device controller 240) may track motion of the blood vessel and automatically adjust the orientation of ultrasound transducer 230 to maintain its focus on the target vessel and to aim at the blood vessel. This tracking may enable continuous monitoring of clinical blood flow parameters such as flow volume, vascular resistance, pressure and rate.

Ultrasound measurement assembly 200 may be used to monitor minimally invasive surgery, e.g., where surgical tools are operated without a direct line of sight by the surgeon. In this case, ultrasound measurement assembly 200 may be placed on the patient's body near the region of the operation, and may provide a continuous ultrasound image of the region of the operation inside the body. The positions of the surgical tools may be tracked, and the orientation and focus of ultrasound transducer 230 may be adjusted accordingly. For example, the image of a surgical tool may be automatically identified and tracked. Similarly, ultrasound measurement assembly 200 may be used to track other foreign objects inserted into the body, such as miniature robots, pill cameras, or endoscopes.

Ultrasound measurement assembly 200 may be used to monitor post-operative and postpartum internal bleeding and/or fluid leakage. For example, ultrasound measurement assembly 200 may be placed on the body surface adjacent to the region of the operation following the operation. Ultrasound measurement assembly 200 may be set up to automatically detect and track irregular blood or fluid concentrations or accumulations, and to monitor their sizes and locations.

Ultrasound measurement assembly 200 may be used to monitor a previously detected tumor inside a patient's body. Following tumor detection or initial treatment, an ultrasound measurement assembly 200 may be periodically and repeatedly placed on the patient's body over the general location of the tumor. Ultrasound measurement assembly 200 may then automatically detect the tumor, and measure its size and accurate location. For example, changes in the tumor's size, shape, and location may be monitored following different treatments in order to evaluate their effectiveness.

Ultrasound measurement assembly 200 may be utilized in combination with a high intensity focused ultrasound (HIFU) system to provide automatic detection, tracking, and ablation of malignant tumors inside the body. In this configuration, both components, the imaging and HIFU transducers, may be co-aligned so as to be focused at the same region. Ultrasound measurement assembly 200 may scan, detect, and track the location and position of a tumor, and the HIFU transducer may focus onto the detected tumor and use ablation to treat or remove it. Ultrasound measurement assembly 200 may then validate the ablation results by tracking the tumor's size and shape after treatment.

Ultrasound measurement assembly 200 may be used to monitor a specific organ failure or insufficiency, e.g., as caused by a reduction in blood flow to the organ. For example, ultrasound measurement assembly 200 may be placed on the body surface near a failing kidney or other failing organ to monitor blood flow to the organ before and after treatment.

Imaging data generated using ultrasound measurement assembly 200 may be registered with previously acquired images of a patient using other imaging modalities (e.g., computed tomography, magnetic resonance imaging, or another modality). Thus, information that is acquired from the different modalities may be overlaid in a single image. For example, an image of a tumor that was identified using a different modality may be overlaid on acquire ultrasound images to assist in identifying a target section.

Data from two or more ultrasound measurement assemblies 200 may be synchronized and combined. For example, data from multiple ultrasound measurement assemblies 200 that are measuring blood flow in different blood vessels, e.g., central and peripheral blood vessels, may be analyzed to determine blood distribution in the circulatory system, calculate a blood pulse transit time (PTT), blood flow into and out of a particular organ, or another result. Ultrasound images that are acquired by two or more ultrasound measurement assemblies 200 at different angles may be processed to construct a three-dimensional representation of a volume within the body.

An ultrasound measurement assembly 200 containing a transducer array and mechanical scanning mechanism may be utilized to generate a three-dimensional representation of a volume inside the body, by mechanically sweeping the ultrasound transducer along an axis that is out of (e.g., perpendicular to) the imaging plane of the ultrasound transducer.

An orientation of an ultrasound measurement assembly 200, or other parameters, may be stored in a data storage unit of, or accessible by, a controller. The stored information may be utilized at a later time to enable another ultrasound measurement assembly 200 to repeat previous measurements (e.g., at the same location or from the same viewing angle as in the previous measurement).

Figure 7:
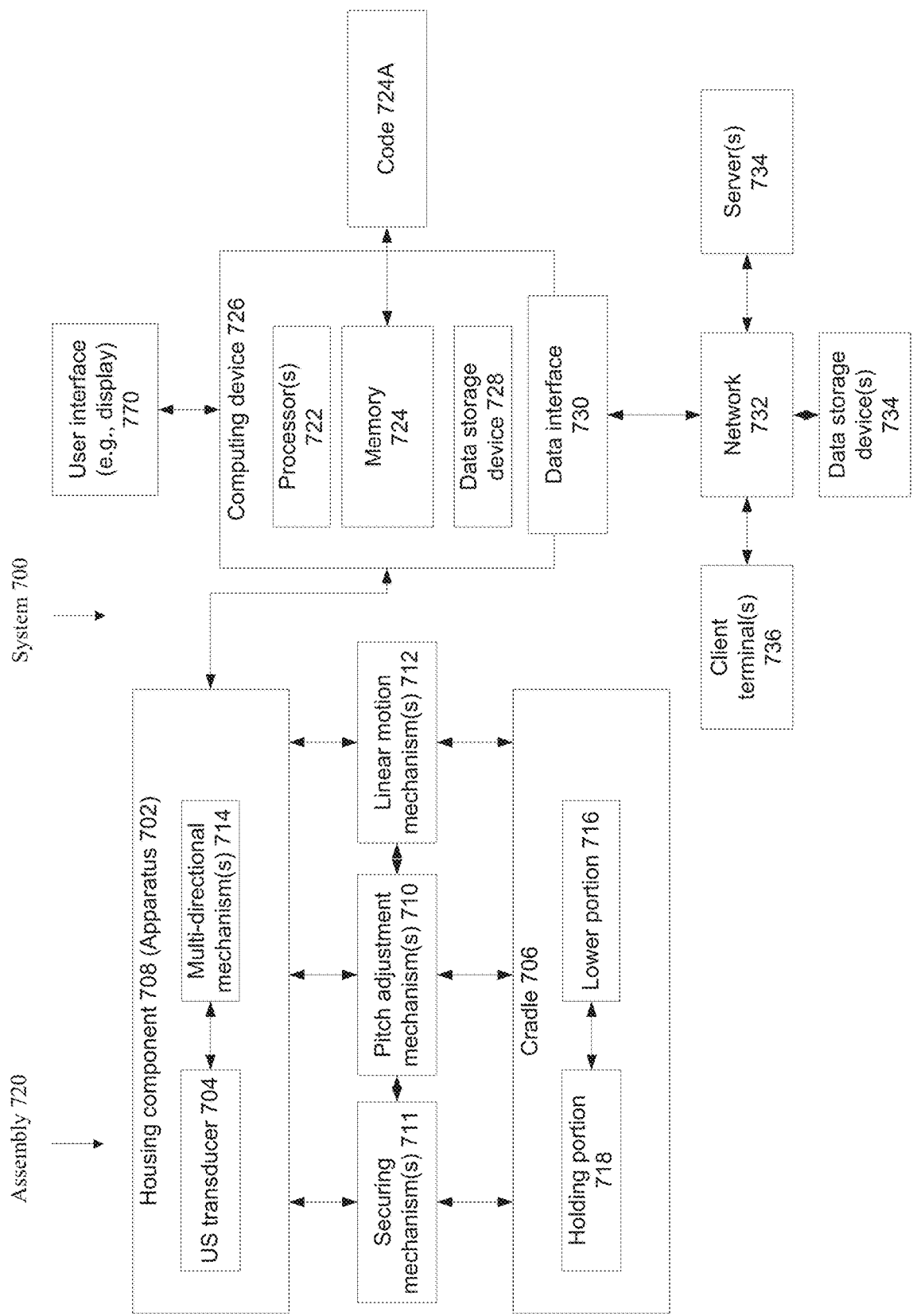
FIG. 7 is a block diagram of a system for hand-free ultrasonic monitoring via a suprasternal notch of a target individual, in accordance with some embodiments of the present invention.

Reference is now made to FIG. 7, which is a block diagram of a system 700 for hands-free ultrasonic monitoring via a suprasternal notch of a target individual, in accordance with some embodiments of the present invention. System 700 includes a housing component 708 which includes therein an ultrasound transducer 704, and a cradle 706 that couples housing component 708 to the suprasternal notch, for hands-free ultrasonic imaging and/or monitoring via the suprasternal notch.

As used herein, the terms ultrasonic imaging and/or monitoring may refer to capture of ultrasound imaging and/or other data computed according to ultrasound energy, for example, hemodynamic monitoring and/or determination of a flow direction (e.g., blood flow within the aorta). The ultrasonic imaging and/or monitoring may be performed continuously, at defined intervals, triggered by events, and/or other methods.

It is noted that one or more components of system 700 may include and/or be based on and/or may be substituted with one or more components of: ultrasonic monitoring system 10 described with reference to FIG. 1, ultrasound measurement unit described with reference to FIGS. 2A-2B, and/or ultrasound measurement assembly described with reference to FIGS. 5A-C and/or FIG. 6.

Housing component 708 stores ultrasound transducer 704. Housing component 708 is designed to fit within cradle 706 that adheres to a skin of an anatomical region that includes the suprasternal notch of the target individual.

Housing component 708 includes a pitch adjustment mechanism 710 and/or a linear motion mechanism 712. Pitch adjustment mechanism 710 adjusts a pitch of the housing component 708 relative to cradle 706. Linear motion mechanism 712 that adjusts a linear position (also referred to herein as linear displacement) of housing component 708 relative to cradle 706 along a linear axis of cradle 706. Is it noted that pitch adjustment mechanism 710 and linear motion mechanism 712 may be implemented as independent mechanisms, or may be integrated into a single mechanism that performs both adjustment features.

A multi-directional mechanism 714 adjusts the position of ultrasound transducer 704 within housing component 708 along at least three degrees of freedom, as described herein.

Optionally, a securing mechanism 711 secures housing component 708 within cradle 716 at a certain pitch and a certain linear displacement.

Cradle 706 includes a lower portion 716 and a holding portion 718. Lower portion 716 includes a surface shaped according to a surface of an anatomical region including a suprasternal notch of at least one sample individual. The surface shape of lower portion 716 may be designed, for example, based on an analysis of a wide range of sample individual, to identify the most common surface features such that lower portion 716 is able to closely adhere to as many target individuals as possible. Alternatively, different lower portions 716 may be designed according to anatomical classifications of sample individuals. Each type of lower portion 716 is designed to fit a certain category of sample individuals, for example, men, women, children, people with deep suprasternal notches, and people with wide suprasternal notches.

Optionally, lower portion 716 includes an adhesive for adhering to the skin of the patient at the anatomical region that includes the suprasternal notch. The adhesive secures cradle 706 to the suprasternal notch, which is a complex, non-flat shape. Optionally, lower portion 716 includes a material (e.g., gel pad and/or equivalent) that provides acoustic coupling between the transducer and body tissue.

Holding portion 718 is shaped to fit and engage housing component 708. Holding portion 718 is sized for providing a pitch range of housing component 708. The pitch range may be defined as above a baseline pitch. Holding portion 718 may be designed to set the baseline pitch, for example, including a pitch element setting the floor pitch of housing 702. For example, one or more prongs located within the interior of holding portion 718, and/or a pitched narrowing of the interior of holding portion 718, that set the lower limit of the pitch. The baseline pitch may be selected relative to the expected shape of the surface area of the suprasternal notch of the target patient. Alternatively or additionally, holding portion 718 is sized for providing a linear displacement range of motion of housing component 708 along a linear displacement axis of holding portion 718.

Assembly 720 refers to housing component 708 coupled to cradle 706 via securing mechanism(s) 711.

Ultrasound transducer 704 may be implemented as one or more of the following:

Phased array.
One dimensional phased array.
Linear phased array.
Two dimensional (2D) phased array.
Non-phased array ultrasound transducer element.
Single ultrasound transducer element.

The orientation and/or position of the phased array implementation of the ultrasound transducer adds additional mechanical degrees of motion, in addition to the electronic degrees of freedom of the phased array. The combination of mechanical degrees of freedom and electronic degrees of freedom provide, for example, for a larger field of view, obtaining image planes in a relatively larger number of different orientations, improved fine tuning for capturing quality ultrasound images, and/or for scanning a volume of tissue for reconstruction of three dimensional ultrasound images. It is noted that in implementations of non-phased array transducers, the position and/or orientation of the non-phased array transducer provides mechanical degrees of motion, for example, for a larger field of view, obtaining image planes in a relatively larger number of different orientations, improved fine tuning for capturing quality ultrasound images, and/or for scanning a volume of tissue for reconstruction of three dimensional ultrasound images.

Optionally, pitch adjustment mechanism 710 and/or linear motion mechanism 712 are manually adjusted and/or manually set by a user. Multi-directional mechanism 714 is automatically adjusted by at least one actuator. Rough adjustment of housing 708 may be performed quickly by manual methods, for example, as an initial setting. Fine precision adjustment may be performed automatically by multi-directional mechanism 714 when searching for anatomical structures and/or monitoring the anatomical structures.

Optionally, pitch adjustment mechanism 710 and/or linear motion mechanism 712 are manually adjusted. Optionally, multi-directional mechanism 714 is automatically adjusted by one or more actuators, optionally under computer control. Rough adjustment may be performed quickly by manual methods, for example, as an initial set-up.

An automatic implementation (e.g., controlled by one or more hardware processors executing code instructions stored in a data storage device and/or instructions implemented in hardware) of multi-directional mechanism 714 provides for a wide search of the anatomical structure, and/or provides fine tuning and/or tracking of the anatomic structure once it is detected.

Multi-directional mechanism 714 is controlled by one or more hardware processors 722 executing code instructions 724A stored in a memory 724. The control of multi-directional mechanism 714 may be according to an analysis of one or more ultrasound signals and/or ultrasound images captured by ultrasound transducer 704, for example, as described herein.

Code 724A may include code for execution of one or more features, for example, continuous ultrasound monitoring as described with reference to FIG. 3A, hemodynamic monitoring as described with reference to FIG. 3B, determination of a flow direction as described with reference to FIG. 4, and/or automatic adjustment of the position of the ultrasound transducer as described with reference to FIG. 10.

Hardware processor(s) 722 and memory 724 may be integrated within housing component 708, for example, as hardware circuitry. Alternatively or additionally, processor(s) 722 and/or memory 724 may be implemented as a computing device 726 in communication (e.g., wireless, wired) with housing component 708. For example, computing device 726 may be implemented as an application loaded on a smartphone (or other mobile device) to control multi-directional mechanism(s) 714 of housing component 708 and/or pitch adjustment mechanism 710 and/or linear motion mechanism 712 and/or securing mechanism(s) 711, code loaded on a server (e.g., monitoring server), an independent component, and/or as a component installed and/or integrated within housing component 708.

Processor(s) 722 may be implemented, for example, as a central processing unit(s) (CPU), a graphics processing unit(s) (GPU), field programmable gate array(s) (FPGA), digital signal processor(s) (DSP), and application specific integrated circuit(s) (ASIC). Processor(s) 722 may include a single processor, or multiple processors (homogenous or heterogeneous) arranged for parallel processing, as clusters and/or as one or more multi core processing devices.

Memory 724 stores code instructions executable by processor(s) 722, for example, a random access memory (RAM), read-only memory (ROM), and/or a storage device, for example, non-volatile memory, magnetic media, semiconductor memory devices, hard drive, removable storage, and optical media (e.g., DVD, CD-ROM). Memory 724 stores code 724A that implements one or more features and/or acts of automatic adjustment of multi-directional mechanism 714 and/or ultrasound image analysis for searching and/or monitoring, as described herein.

Computing device 726 may include and/or be in communication with a data storage device 728, for example, for storing acquired ultrasound images and/or ultrasound templates (e.g., as described herein). Data storage device 728 may be implemented as, for example, a memory, a local hard-drive, virtual storage, a removable storage unit, an optical disk, a storage device, and/or as a remote server and/or computing cloud (e.g., accessed using a network connection).

Computing device 726 may include a data and/or network interface 730 for connecting to a network 732, for example, one or more of, a network interface card, a wireless interface to connect to a wireless network, a physical interface for connecting to a cable for network connectivity, a virtual interface implemented in software, network communication software providing higher layers of network connectivity, and/or other implementations. Network 732 may be implemented as, for example, the internet, a local area network, a wireless network, a cellular network, a local bus, a point to point link (e.g., wired), and/or combinations of the aforementioned. Computing device 726 may connect using network 732 (or another communication channel, such as through a direct link (e.g., cable, wireless) and/or indirect link (e.g., via an intermediary computing unit such as a server, and/or via a storage device) with one or more of:

- Data storage device(s) 734 (e.g., server), for example, for uploading the acquired ultrasound-based images and/or data, and/or downloading new code for controlling multi-directional mechanism 714.
- Client terminals 736 and/or server 738, for example, for remote monitoring of the performance of assembly 720 and/or for remote viewing of acquired ultrasound based data.

Optionally, assembly 720 (e.g., housing 708 and/or cradle 706) include a set of a fixed photodiode gate and a needle defining a reference zero position for calibrating each axis of motion of multi-directional mechanism 714 and/or pitch adjustment mechanism 710 and/or linear motion mechanism 712. Motion occurring along each available axis is relative to the reference zero point. The assembly 720 may be calibrated along each axis of motion, for control of fine movements of the housing 708 and/or ultrasound transducer 704 when searching for anatomical structure(s) and/or monitoring the anatomical structure(s).

Computing device 726 and/or housing component 708 may include and/or be in communication with a user interface 770 that includes a mechanism for a user to enter data (e.g., define position of the ultrasound transducer, start automatic monitoring) and/or view presented data (e.g., acquired image(s), collected data, current position(s) of ultrasound transducer). Exemplary user interfaces 770 include, for example, one or more of, a touchscreen, a display, a keyboard, a mouse, and voice activated software using speakers and microphone. External devices, such as client terminals 736 and/or server(s) 734 communicating with computing device 726 and/or housing component 708 (e.g., via network 732) may serve as user interface 770, for example, a smartphone running an application may establish communication (e.g., cellular, network, short range wireless) with computing device 726 and/or housing 708 (e.g., over network 732) using a communication interface (e.g., network interface, cellular interface, short range wireless network interface). The user may enter data and/or view data on the display of the smartphone, optionally via a graphical user interface (GUI) application.

Reference is now made to FIGS. 8A-8F, which are schematics depicting an exemplary implementation of an assembly 820, including housing component 808 and/or cradle 806, based on assembly 720, housing component 708 and/or cradle 706, as described with reference to FIG. 7, in accordance with some embodiments of the present invention.

Figure 8A:
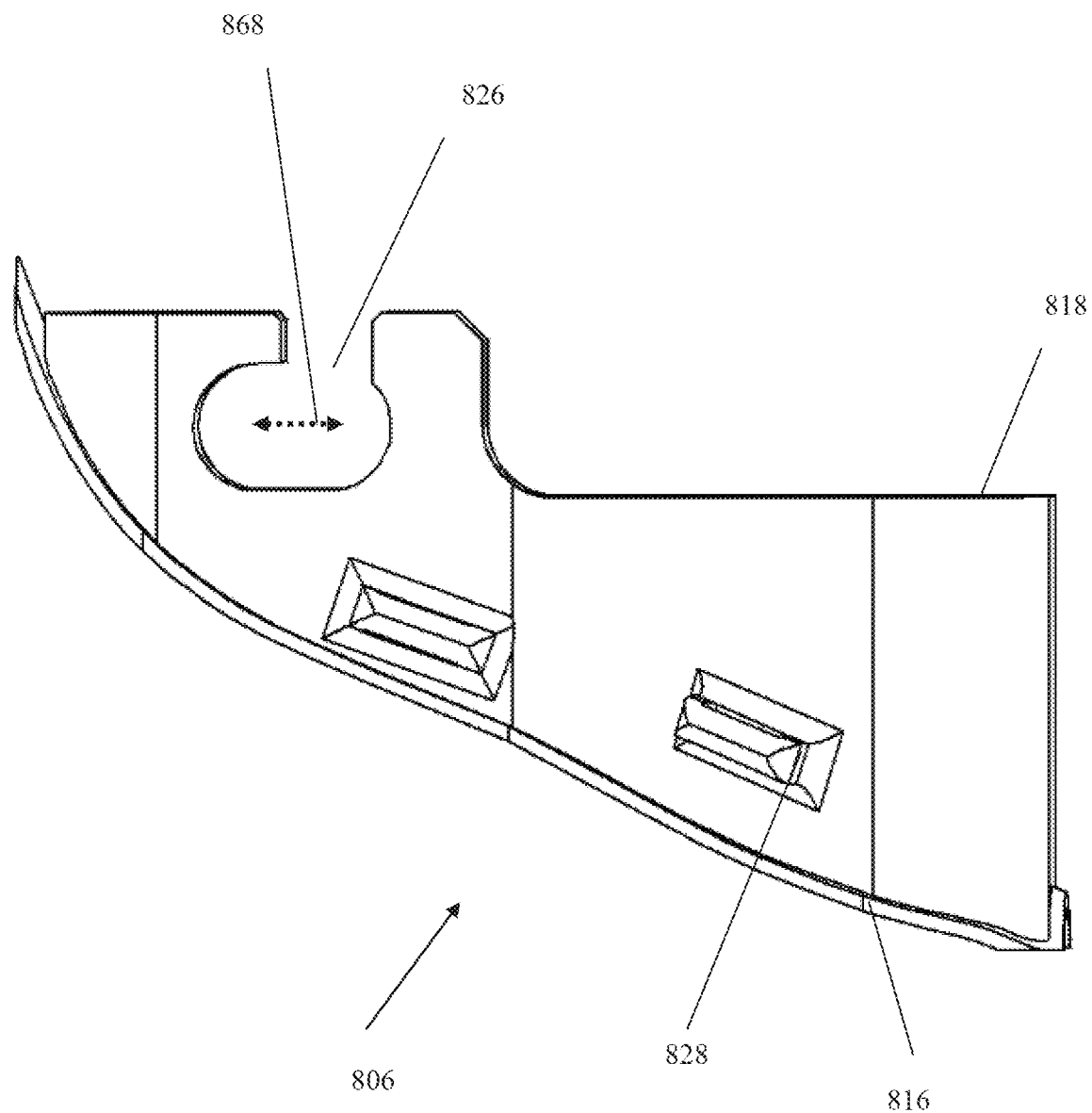
FIGS. 8A-8F are schematics depicting an exemplary implementation of an assembly including a housing component and/or cradle for hand-free ultrasonic monitoring via a suprasternal notch of a target individual, in accordance with some embodiments of the present invention.

FIG. 8A is a schematic depicting a side view of an exemplary implementation of cradle 806, shown in use when adhered to the skin of the target individual for imaging via the suprasternal notch of the target individual (neck of target individual is omitted for clarity). Cradle 806 connects to a housing component 808 (shown in other Figs) to form assembly 820 for hands-free ultrasonic imaging via the suprasternal notch of the target individual.

Cradle 806 includes a lower portion 816 having a surface shaped according to a surface of an anatomical region including a suprasternal notch of at least one sample individual. The surface of lower portion 816 may be designed to fit a wide range of individuals based on an analysis of the anatomical features of the sample individuals, and/or may be designed to fit certain populations of individuals based on distinct anatomical features of each population (e.g., men, women, children, neck side, depth of suprasternal notch.

Cradles includes a holding portion 818 shaped to fit housing component 808. Holding portion 818 is sized for providing: a pitch range for housing component 808 and a linear displacement range of motion 868 for housing component 808. The pitch range may be defined above a baseline pitch. The baseline pitch may be set as substantially corresponding to a pitch of the suprasternal notch when cradle 806 is connected to housing 808 and when assembly 820 is adhered to the skin of the patient while in use. The baseline pitch may be set approximately (within a tolerance) according to the pitch of the surface of lower portion 816. The linear displacement range of motion may be set along a linear displacement axis of holding portion 818. The linear displacement axis may be set to be at a predefined angle within a tolerance) relative to the pitch of the surface of the suprasternal notch and/or the pitch of the surface of lower portion 816, for example, about 15-60 degrees, or about 30-45 degrees or other values. The predefined angle may be selected approximately (within a tolerance) according to the initial angle between the ultrasound transducer and the surface of the suprasternal notch for imaging the target internal anatomical structures (based on an analysis of other sample individuals). The linear displacement axis may be set to be approximately parallel to the floor when assembly 820 is in use on a target patient sitting or standing.

Optionally, holding portion 818 includes one or more elongated slots 826, optionally one on each side of holding portion 818. Each elongated slot 826 engages a securing mechanism of housing component 808 for securing housing component 808 within cradle 806 at a certain pitch and a certain linear displacement. Securing mechanism may be integrated with pitch adjustment mechanism 710 and/or linear motor mechanism 712.

Each elongated slot 826 is elongated along the linear displacement axis to provide the linear displacement range. Securing mechanism of housing component 808 engages each elongated slot 826 via a channel opening. The elongated slot(s) makes it easy to connect housing component 808 to cradle 806, correctly aligns housing component 808 relative to cradle 806, and makes it easy for a user to set the pitch and/or linear displacement.

The linear displacement axis is approximately (within a tolerance) parallel to an axis defining the baseline pitch. The baseline pitch is substantially parallel to the surface of the suprasternal notch. The linear displacement is parallel to the baseline pitch to position the ultrasound transducer over the suprasternal notch.

The linear displacement axis is set to fit the anatomy of a large range of target individuals that vary anatomically. Even when the fit is off, the housing component 808 may be further adjusted according to the specific anatomy of the target individual such the described adjustment mechanisms.

Optionally, cradle 806 includes one or more handles 828 located on the exterior surface of the cradle for connecting a strap. The handles 828 may be arranged in pairs on opposing sides of the cradle, corresponding to the left and right sides of the patient when in use. The strap may be wrapped around the neck of the patient, positioning cradle 806 against the skin of the patient. The strap may be used in addition to, or in place of the adhesive layer described here that adheres the assembly to the skin of the patient. Handles 828 may include a strap locking mechanism to secure the strap, for example, a buckle, a button that inserts into a slit of the strap, Velcro that adheres to corresponding portions of the strap, a zipper end, and/or clips that tightly adhere to the strap.

Figure 8B:
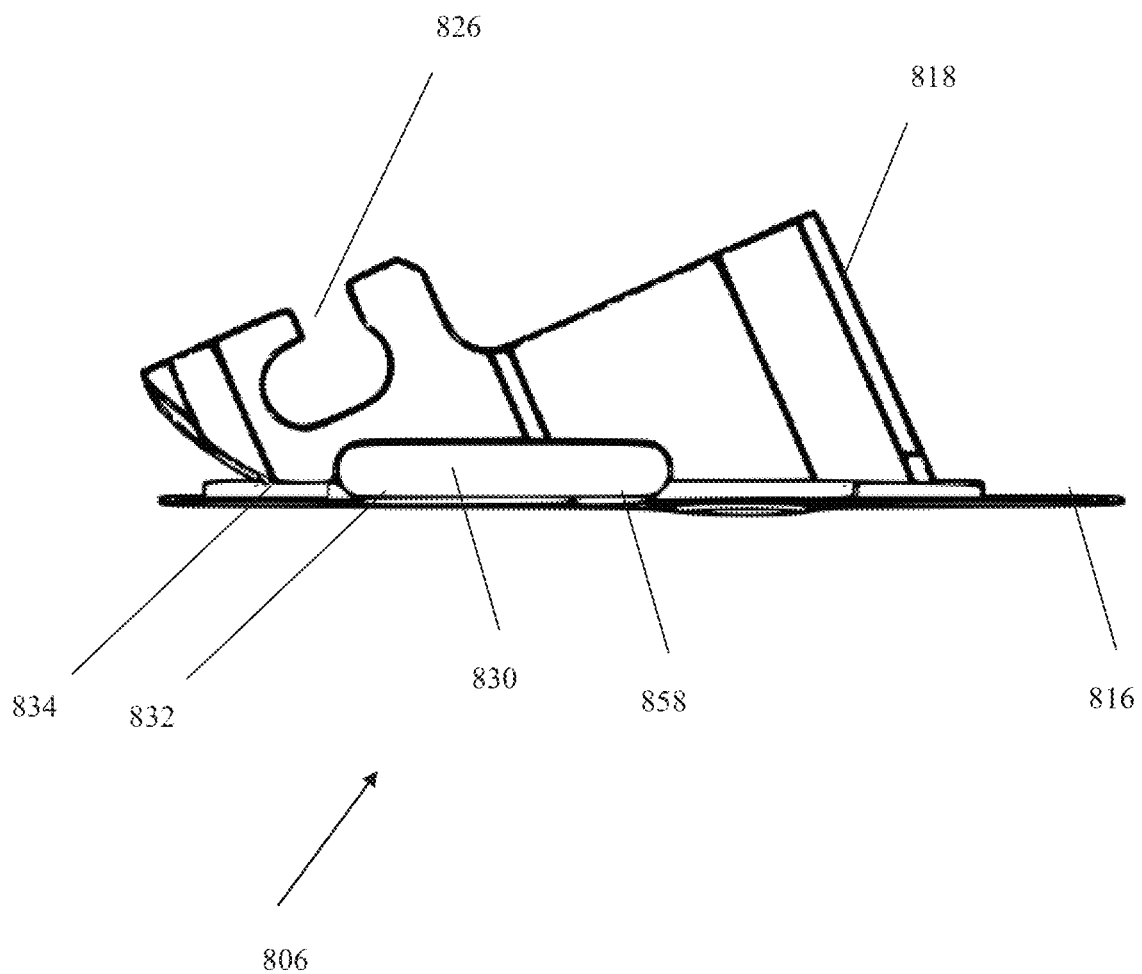

FIG. 8B is a schematic depicting a cross sectional view of an exemplary implementation of cradle 806, shown prior to application to the skin of the target individual, for example, lying flat on a surface such as during storage. Cradle 806 includes an acoustic window 858, optionally an orifice within lower portion 816 (i.e., to prevent interference of transmission of ultrasound energy via acoustic window 858). An acoustic transmission material 830 (e.g., gel) is located within acoustic window 858, optionally enclosed within a compartment 832. Acoustic window 858 may be sized to correspond to a size of the suprasternal notch of at least one sample individual, for example, at least as large as the size of the suprasternal notch, and/or corresponding to the size of the suprasternal notch within a tolerance.

Compartment 832 is located within acoustic window 858. A bottom surface of compartment 832 is set to contact the skin of the suprasternal notch when in use. An upper surface (opposite the lower surface) of compartment 832 contacts the ultrasound transducer 804 of housing component 808 (shown in other Figs) when housing component 808 is connected to cradle 806. Compartment 832 fills a gap between ultrasound transducer 802 and the surface of the suprasternal notch with an acoustic matching layer material (e.g., ultrasound gel).

Optionally, the bottom surface of compartment 832 is shaped according to a surface of the suprasternal notch of at least one sample individual, for example, based on an analysis of the most common shape of a population of individuals, and/or multiple shapes may be designed each for a certain sub-population (e.g., depth, surface area, and/or length of the suprasternal notches for each sub-population). The shape of compartment 832 is designed to reduce or eliminate air bubbles between compartment 832 and the surface of the suprasternal notch. The quality of the ultrasound images captured by the ultrasound transducer is improved by the absence or reduction of air bubbles in the ultrasound wave path.

Optionally, the bottom surface of compartment 832 includes an adhesive for adhering to the surface of the suprasternal notch. The adhesive surface on the bottom surface of compartment 832 eliminates or reduces the formation and/or presence of air gaps, optionally air bubbles between the bottom surface of compartment 832 and the surface of the suprasternal notch.

Optionally, bottom portion 816 of cradle 806 includes a flexible material 834 that matches to the shape of the body surface of the target individual when pressed towards the body surface (in use), for example, foam, and/or silicon.

Flexible material 834 matches its shape to the body surface (i.e., skin region in proximity to the suprasternal notch) when cradle 806 is pressed towards the body surface. The matching of the shape of flexible material 834 to the body surface increase the total surface area of cradle 806 in contact with the skin (e.g., in comparison to a more rigid material). The matching of the shape of flexible material 834 to the body surface reduces or eliminates the formation of air bubbles between flexible material 834 and the body surface. The air bubble formation is reduced or prevented when flexible material 834 matches in shape to the body and/or attaches smoothly to the body surface. The presence of air bubbles reduce the quality of the transmission of the ultrasound energy.

Figure 8C:
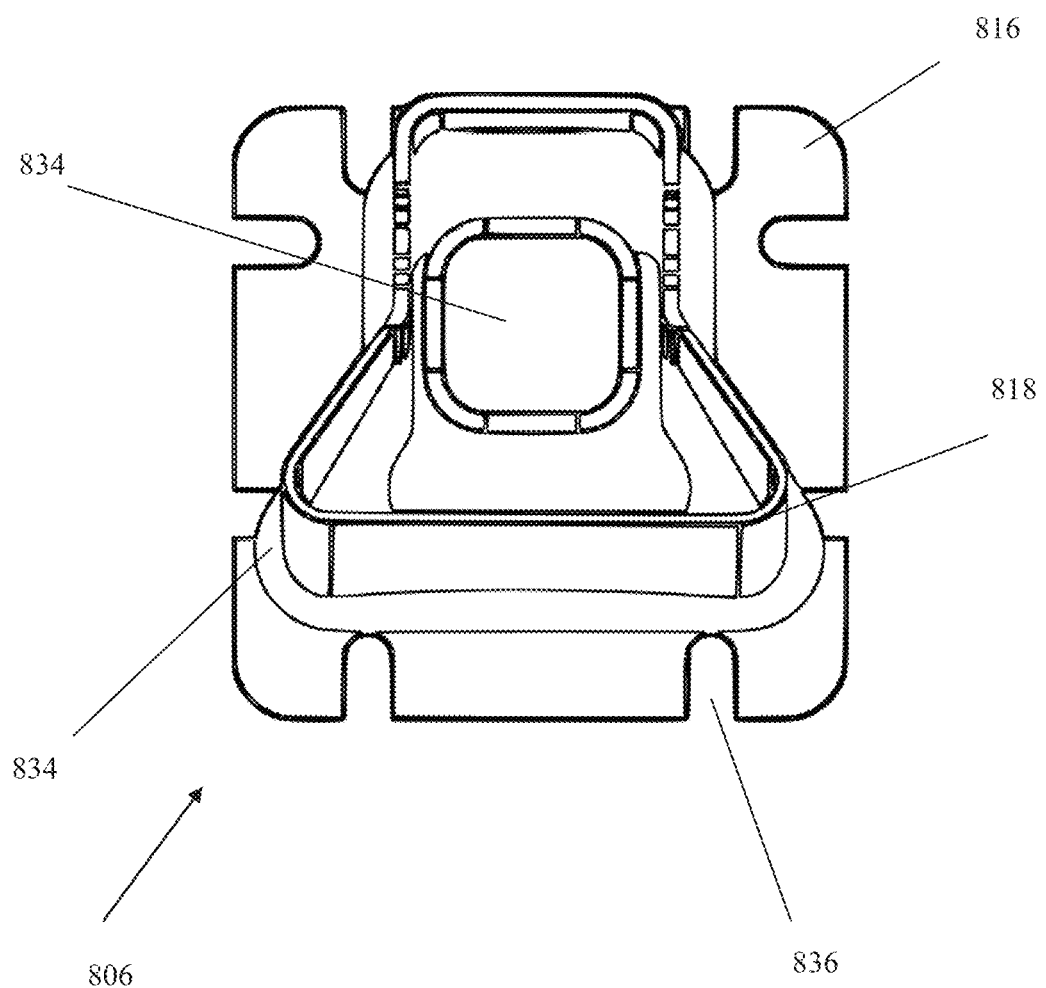

FIG. 8C is a schematic depicting a top view of an exemplary implementation of cradle 806.

Optionally, wherein lower portion 816 of cradle 806 is larger than the area of holding portion 818 coupled to lower portion 816. The region of lower portion 816 larger than the area of holding portion 818 is shaped to fit the anatomical region surrounding the suprasternal notch. The region larger than the area of the holding portion provides a sufficient attachment force to the anatomical region surrounding the suprasternal notch. The attachment force is selected to endure the forces produces by the motion of mechanisms of the housing component and/or the pressured applied to the ultrasound transducer against the suprasternal notch, as described herein.

Optionally, lower portion 816 includes one or more slots 836 extending from an edge of lower portion 816 towards holding portion 818, for example, two or more slots 836 per approximately rectangular shape of lower portion 816. Slots 836 are designed to prevent or reduce stress in lower portion 816, folding over of parts of lower portion 816, elevations of parts of lower portion 816, which may other occur when lower portion 816 (without slots 836) is fitted to the irregular skin surface of the neck of the target individual.

Figure 8D:
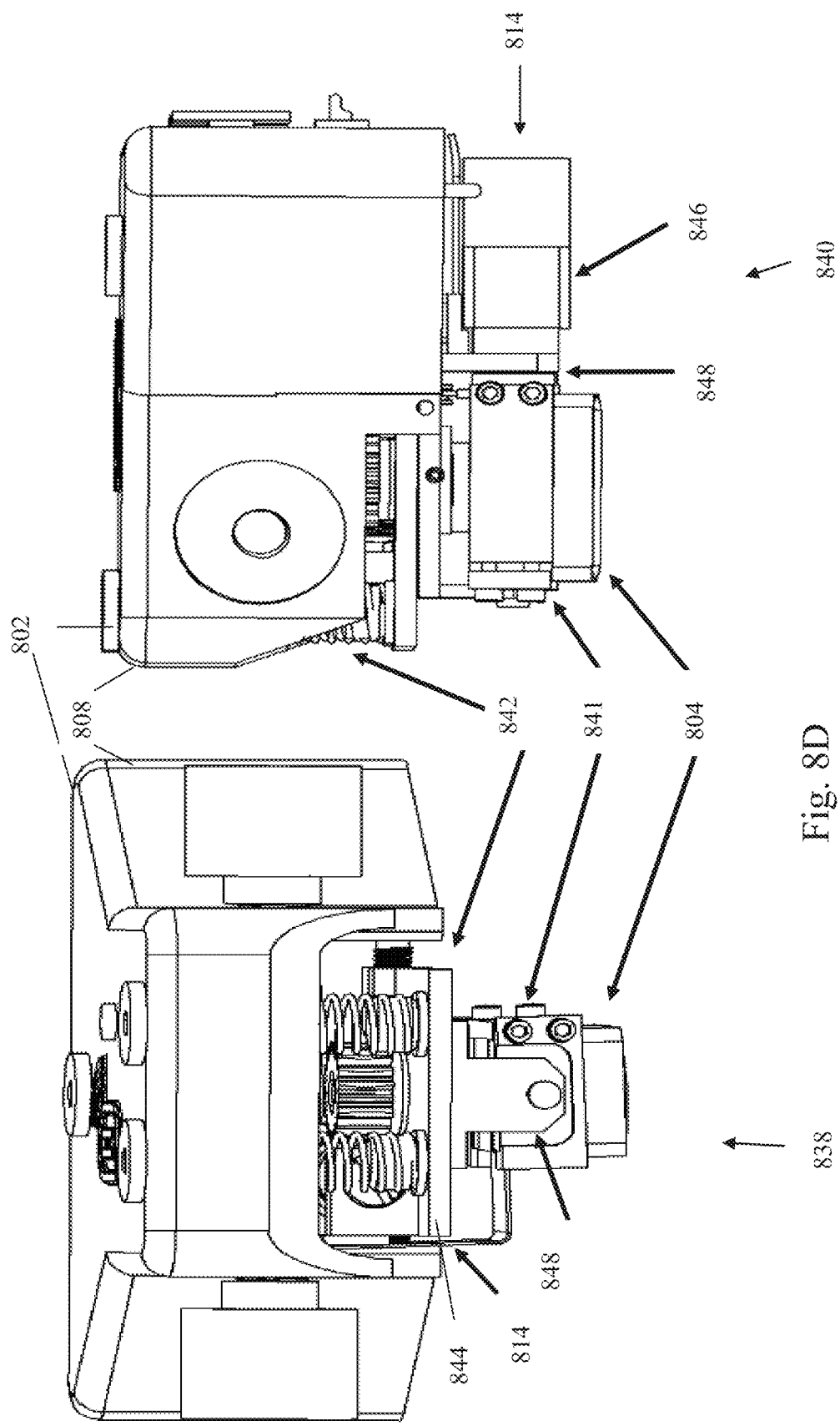

FIG. 8D is a schematic depicting a front view 838 and a side view 840 of an exemplary implementation of housing component 808.

Housing component 808 stores ultrasound transducer 804. Ultrasound transducer 804 may be implemented as one or more of the following:
Phased array.
One dimensional phased array.
Linear phased array.
Two dimensional (2D) phased array.
Non-phased array ultrasound transducer element.
Single ultrasound transducer element.

Transducer 804 may be held by an ultrasound transducer holder 841. Housing component 808 is designed to fit within cradle 806.

Housing component 808 includes a multi-directional mechanism 814 for adjusting the position (e.g., orientation, location within space) of ultrasound transducer 804 along at least three degrees of freedom. Multi-directional mechanism 814 includes at least one resilient element 842 (e.g., spring (s), actuators, memory metal (e.g., nitinol) based elements, and/or bellows) set to provide linear motion of ultrasound transducer 804 along a vertical axis of housing component 808, for example, about 10, 15, 20, or 25 millimeters (mm) or other values. Resilient element(s) 842 enable hands-free operation of assembly 720, by providing pressure to apply ultrasound transducer 804 against the suprasternal notch. Such pressure which would otherwise be applied by a human operator which presses the ultrasound probe towards the body. Moreover, resilient element 842 applies an adjustable pressure, which helps ensure and/or maintain constant and/or uniform contact between ultrasound transducer 804 and the gel pad (e.g., compartment 834), even when ultrasound transducer 804 is rotated. Optionally, resilient element (s) presses 842 ultrasound transducer 804 within compartment 834 housing acoustic transmission material, such that ultrasound transducer 804 maintains contact with the surface of compartment 804 housing acoustic transmission material during motion within the at least three degrees of motion provided by multi-directional mechanism 814. When housing component 808 is connected to cradle 806 and in use (i.e., adhered to the skin of the suprasternal notch), resilient element(s) 842 apply pressure to ultrasound transducer 804, such that ultrasound transducer 804 maintains contact with the surface of compartment 834 housing the acoustic transmission material throughout the ultrasound monitoring processes, during motion of ultrasound transducer 804 within the at least three degrees of motion.

Optionally, resilient element(s) 842 may include, for example, one or more springs, actuators, memory metal (e.g., nitinol) based materials, and/or bellows, having a first end portion connected to housing component 808 and a second end portion connected to a top surface of a support (e.g., flat plate) 844. Ultrasound transducer 804 is connected to the bottom surface of flat plate 844, optionally indirectly connected via holder 841 of transducer 804. The spring(s) 842 are arranged along a vertical axis of housing component 808. Spring(s) 842 are set for urging ultrasound transducer 804 along the vertical axis of housing component 808.

As used herein, the term spring (e.g., spring(s) 842) is meant as an exemplary implementation of the resilient element. It is understood that other implementations are possible, for example, actuator(s), memory metal (e.g., nitinol) based materials, and/or bellows.

Optionally, three springs 842, or other number of springs (e.g., 4, 6) are implemented, located at positions along the flat plate 844 to perform substantially even urging of the plate. For example, two springs at the left and right portions of the front of the plate and a single spring towards the back portion of the plate. In another example, one spring at each of the four corners of the flat plate.

It is noted that the shape of flat plate 844 is designed according to the shape of the housing and/or holding portion of the cradle, for example, rectangular, trapezoid, square, or other shapes.

Optionally, the resilient element(s) 842 are located internally within housing component 808 at a location approximately corresponding to an external location of securing mechanism (e.g., screw 811, or other securing element implementation, for example, a clip, spring, gear) located on one or both external side surfaces of housing component 808. Screw 811 may be located along a horizontal axis of housing component 808, which may correspond to the medial-lateral axis relative to the patient when assembly 820 is in use. The corresponding locations of resilient element(s) 842 and screw 811 provide for urging of ultrasound transducer 804 along a vertical axis of housing component 808 that is perpendicular to the vertical axis of screw 811. The orientation of the vertical axis is according to the selected pitch and/or linear displacement of housing component 808 that is secured by screw 811 tightening against cradle 806.

The spring(s) enables selection of a suitable spring constant. The spring constant is selected to urge ultrasound transducer towards the suprasternal notch with a pressure requirement that provides quality ultrasound images. The spring constant is selected (e.g., experimentally, and/or based on a computed model) according to an identified minimal amount of applied pressure at which high quality ultrasound images may be acquired in a wide range of sample individuals and/or in one or more defined subpopulations.

Plate 844 may hold one or more additional components of multi-directional mechanism 814, for example, motors and/or shafts and/or gears described herein.

Multi-directional mechanism 814 includes a tilting actuator 846 for tiling ultrasound transducer 804 along a roll axis (i.e., tilting axis) 848, providing, for example, a roll range of about 20, 30, 40, degrees, or other values. Roll axis 848 may be arranged in parallel to a longitudinal axis (i.e., front-back) of housing compartment 802. Ultrasound transducer 804 is tilted to a left and right of the patient (i.e., medially and/or laterally to the patient) when assembly 820 is in use. Tilting actuator 846 may include a tilting micro stepper motor connected to housing component 802 and a tilting motor shaft 848 connected at one end thereof to support (e.g., plate) 844 connected to ultrasound transmitted 804, and connected at an opposite end thereof to the tilting motor.

Optionally, tilting actuator 846 is located on a bottom surface of flat plate 844. The top surface of flat plate 844 is connected to one end of resilient element(s) (e.g. spring(s)) 842. An opposite end of resilient element(s) (e.g., spring(s)) 842 is connected to housing 808. The resilient element(s) 842 linearly urges the flat plate 844 and connected tilting actuator 846 along a vertical axis of housing component 808. The design in which the tilting actuator is attached to a flat plate that is urged by the resilient element(s) (e.g., springs) provides for tilting of the ultrasound transducer independently of the linear displacement of the flat plate by the springs.

Optionally, tilting actuator 846 is arranged in parallel to a longitudinal axis of housing component 808. The tilting actuator 846 may be located along the bottom of the housing component 808 and/or attached to the bottom surface of flat plate 844. The arrangement of the tilting actuator in parallel to the longitudinal axis of the housing component provides for a compact design in which the tilting actuator fits within the cradle when the housing is engaged with the cradle, and/or the tilting actuator does not reduce or prevent the selected range of motion of the ultrasound actuator along the defined degrees of freedom.

Optionally, support (e.g., plate) 844, tilting motor shaft 848, and the tilting motor of tilting actuator 846 are arranged along a linear axis substantially parallel to the longitudinal axis of housing component 802.

Figure 8E:
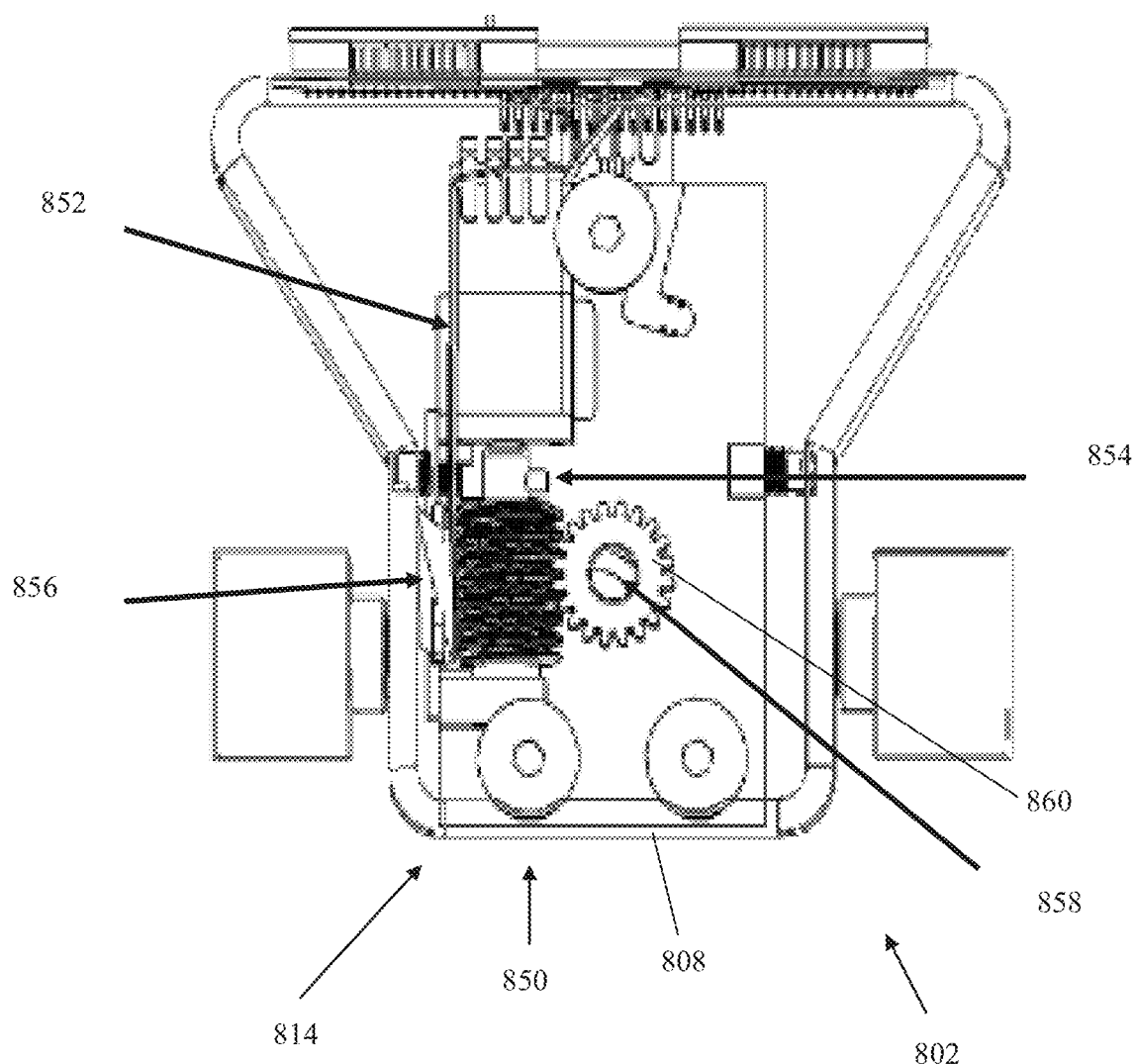

FIG. 8E is a schematic depicting a top view of an exemplary implementation of housing component 808. Multi-directional mechanism may include a rotation actuator 850 for rotating ultrasound transducer 804 along a yaw axis (e.g., rotation axis) 858 arranged in parallel to a vertical axis (i.e. up-down) of housing component 808. Ultrasound transducer 804 is rotated anteriorly and/or posteriorly to the patient when the assembly 820 is in use. The ultrasound transducer is arranged perpendicular to the roll axis. Rotation actuator 850 may include a rotation micro stepper and/or geared motor 852 coupled to one end portion of a motor shaft 854. The opposite end portion of motor shaft 854 is coupled to a worm gear 856.

Optionally, rotation micro stepper motor 852, motor shaft 854, and/or worm gear 856 are arranged along a linear axis (i.e., longitudinal mid-line) of housing component 808 substantially parallel to the longitudinal axis of housing component 808. Rotation micro stepper motor 852, motor shaft 854, and/or worm gear 856 are aligned along a longitudinal axis located in parallel to the mid-line and to the left or right of a centrally located longitudinal axis. Worm gear 856 may be meshed to a gear 858 of a rotational shaft 860 located along a vertical axis (i.e., up-down) of housing component 808. Rotational shaft 860 may be coupled to support 844 of ultrasound transducer 804. Optionally, rotational shaft 860 extends through the flat plate 844 to connect to the holder 841 of the ultrasound transducer 804. Rotation micro stepper motor 852, motor shaft 854, and/or worm gear 856 are located within housing 808. The location of rotation micro stepper motor 852, motor shaft 854, and/or worm gear 856 to the left or right of the centrally located rotational shaft 860 provides delivery of strong torque to rotate the ultrasound transducer 804 via rotational shaft 860.

Optionally, rotation actuator 850 is located on a top surface of the flat plate 844. The top surface of flat plate 844 is connected to one end of resilient element(s) 842 (e.g., springs). An opposite end of resilient element(s) is connected to housing 808. The resilient element(s) 842 (e.g., springs) linearly urge flat plate 844 and connected rotation actuator 850 along a vertical axis of housing component 808. The design in which the rotation actuator is attached to the flat plate that is urged by the resilient element(s) (e.g., springs) provides for rotation of the ultrasound transducer independently of the linear displacement of the flat plate by the springs.

Rotational actuator 850 is designed to provide a torque sufficient to overcome frictional forces and rotate ultrasound transducer 804 when ultrasound transducer 804 is urged by resilient element(s) 842 towards the suprasternal notch. The torque is selected to overcome frictional forces between ultrasound transducer 804 and compartment 834 in contact with the suprasternal notch. The applied torque moves ultrasound transducer 804 smoothly when ultrasound transducer 804 is pushed by resilient element(s) 842 towards the suprasternal notch. Worm gear 856 increases the torque along the axis of rotation. Optionally, the torque is about 10, 12, 14, 16, 18 kg*cm (kilogram*centimeter), or other values.

Rotational actuator 850 is set for rotating ultrasound transducer 804 along the yaw axis (relative to housing 808) within a range of about 40, 60 or 80 degrees, or other values. The range is selected to enable imaging of the anatomical structures via the suprasternal notch for a wide range of target individuals that vary anatomically.

Figure 8F:
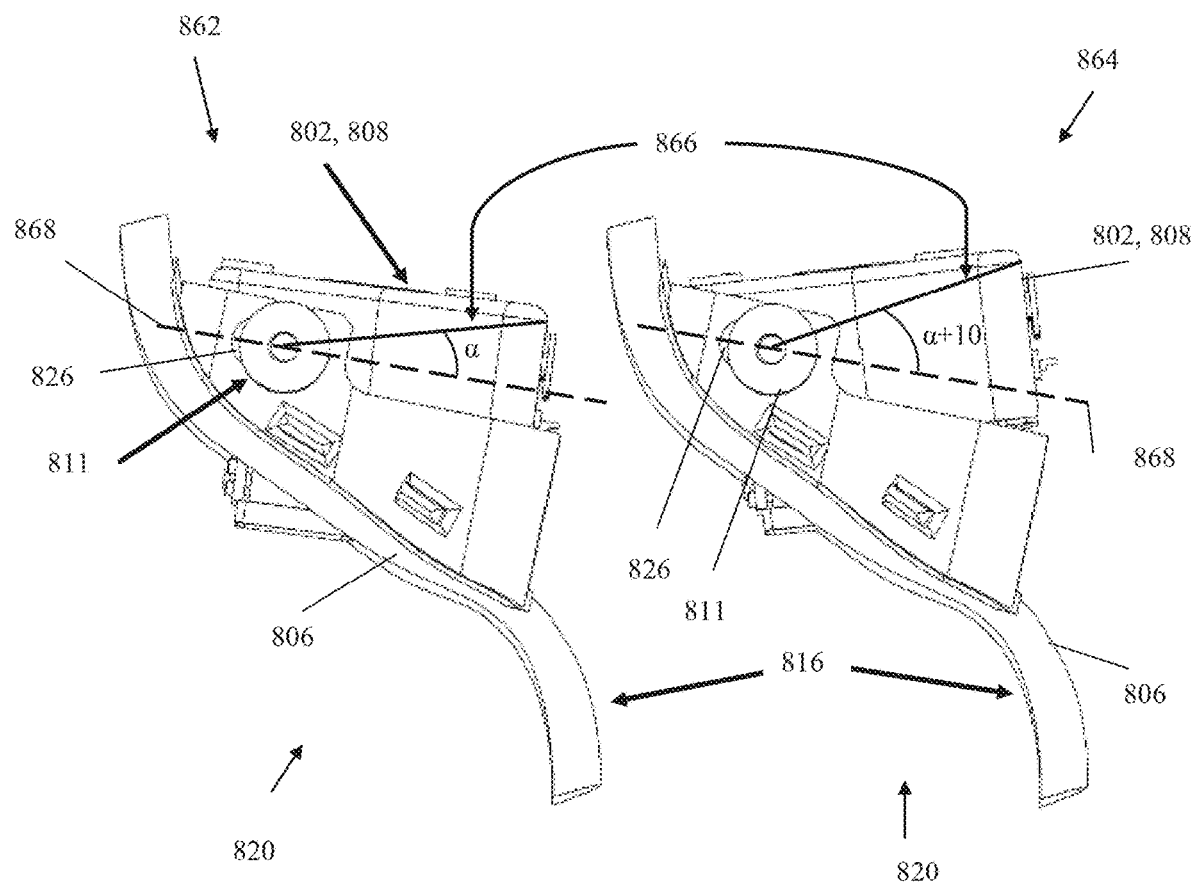

FIG. 8F is a schematic depicting an exemplary implementation of assembly 820, in which housing component 808 is connected to cradle 806. Schematic 862 depicts housing component 808 at an initial baseline relative to a linear axis of cradle 806. The baseline angle is denoted alpha (α). Schematic 864 depicts housing component 808 at a maximal pitch angle (e.g., about 10 degrees) relative to the initial baseline (α+10). Arrow 866 denotes the range of pitch of housing component 808.

Exemplary dimensions of housing component 808 are less than about 65 mm×70 mm×30 mm, or less than about 60 mm×60 mm×25 mm, or less than about 70 mm×80 mm×35 mm, or other values. The dimensions are selected to reduce or prevent interference with movement of the neck. The components of the housing component 808, including actuators (e.g., motors) are designed to fit within the dimensions of housing component 808, for example, motors and/or other components (e.g., gears, shafts) described herein may having dimensions smaller than about 10 mm (e.g., diameter, and/or length).

Optionally, the pitch adjustment mechanism 710 and the linear motion mechanism 714 (described with reference to FIG. 7) are implemented by elongated slot 826 of cradle 806 and a securing element (e.g., screw 811 implementation, clip, locking gear) of securing mechanism 711 of housing component 808. As used herein, screw 811 represents an exemplary implementation of the securing element of the securing mechanism, however, it is to be understood that other implementations are possible, for example, clips, and locking gears. Screw 811 secures housing component 808 within cradle 806 at a selected pitch and/or a selected linear displacement by securing at a corresponding location within elongated slot 826.

Optionally, the screw 811 implementation of securing mechanism 711 provides a single mechanism for simultaneous securing of both the selected pitch and the selected linear displacement. The screw 811 implementation of securing mechanism 711 may be manually adjusted, quickly, and/or by users with little training and/or little experience.

Linear motion mechanism 712, optionally implemented as screw 811, for adjusting a linear displacement of housing component 808 relative to cradle 806 along a linear axis (i.e., front-back) 868 of cradle 806 defined by elongated slot(s) 826. It is noted that two screws 811 may be implemented, one on each side of housing 808. Linear axis 868 is substantially parallel and/or at a defined angle (within a tolerance) to lower component 816 of the casing component. Linear axis 868 guides the urging of housing component 808 towards the surface of the suprasternal notch, for positioning of ultrasound transducer 804 for imaging via the suprasternal notch. Linear motion mechanism 712, optionally screw(s) 811, is designed for adjusting the position of housing component 808 within a range of about 5, 10, 15, 20 millimeters (mm) or other values along linear axis 868. The 10 mm (or other selected value) is designed to account for anatomical variations of target individuals.

Pitch adjustment mechanism 710, optionally implemented as screw(s) 811, is designed for adjusting a pitch of housing component 808 relative to cradle 806. Pitch extremes, at alpha and alpha+10, are depicted respectively with reference to schematics 862 and 864 the pitch adjustment mechanism adjusts the pitch of the housing component relative to linear axis 858 and/or the lower surface of lower component 816 of cradle 806. The pitch adjusts the angle at which the ultrasound transducer images anatomical structures via the suprasternal notch, providing for imaging of anatomical structures located at different positioned within the body, and/or providing for imaging of target individuals with anatomical variations in the locations of the anatomical structures. Pitch adjustment mechanism 710, optionally screw(s) 811, is designed for securing the selected pitch position between housing component 808 and cradle 806. The pitch is adjustable for example, within a range of about 10-15, or 10-25, or 15-30 degrees, or other values. The degree range of adjustment is selected to account for anatomical variations of individuals.

Figure 9:
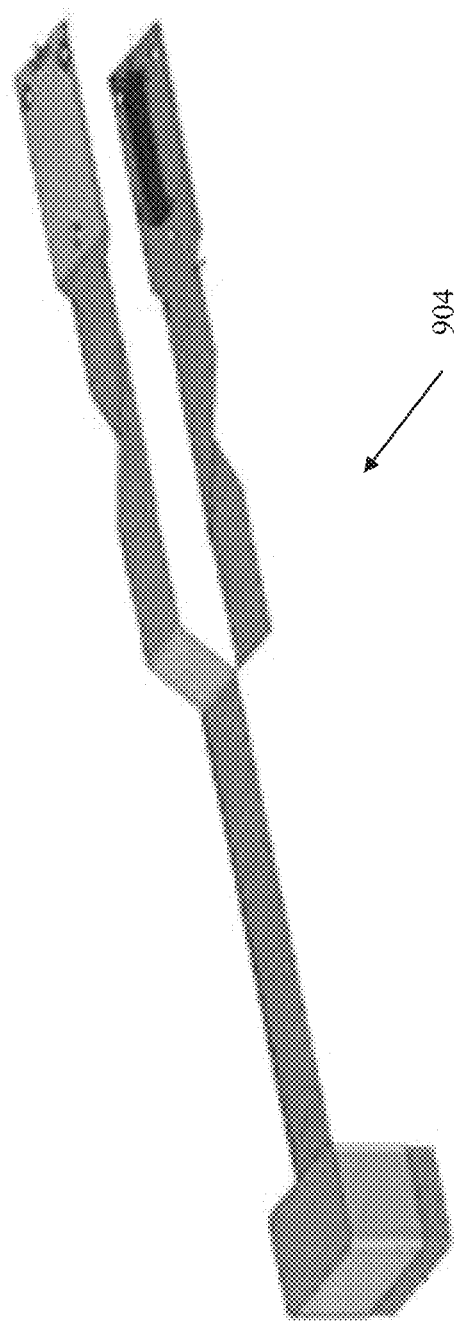
FIG. 9 is a schematic depicting an exemplary implementation of a single ultrasound transducer element of an assembly for hand-free ultrasonic monitoring via a suprasternal notch of a target individual, in accordance with some embodiments of the present invention.

FIG. 9 is a schematic depicting an exemplary implementation of a one dimensional phased array ultrasound transducer element 904 of a housing component (e.g., as described with reference to FIGS. 7 and/or 8A-F) for hands-free ultrasonic monitoring via a suprasternal notch of a target individual, in accordance with some embodiments of the present invention. The orientation and/or position of the single transducer element is adjusted directly by the multi-directional mechanism and/or indirectly by the pitch adjustment mechanism and/or the linear motion mechanism, which provides improved image quality and/or field of view in comparison to electronic adjustment of a fixed phased array.

Figure 10:
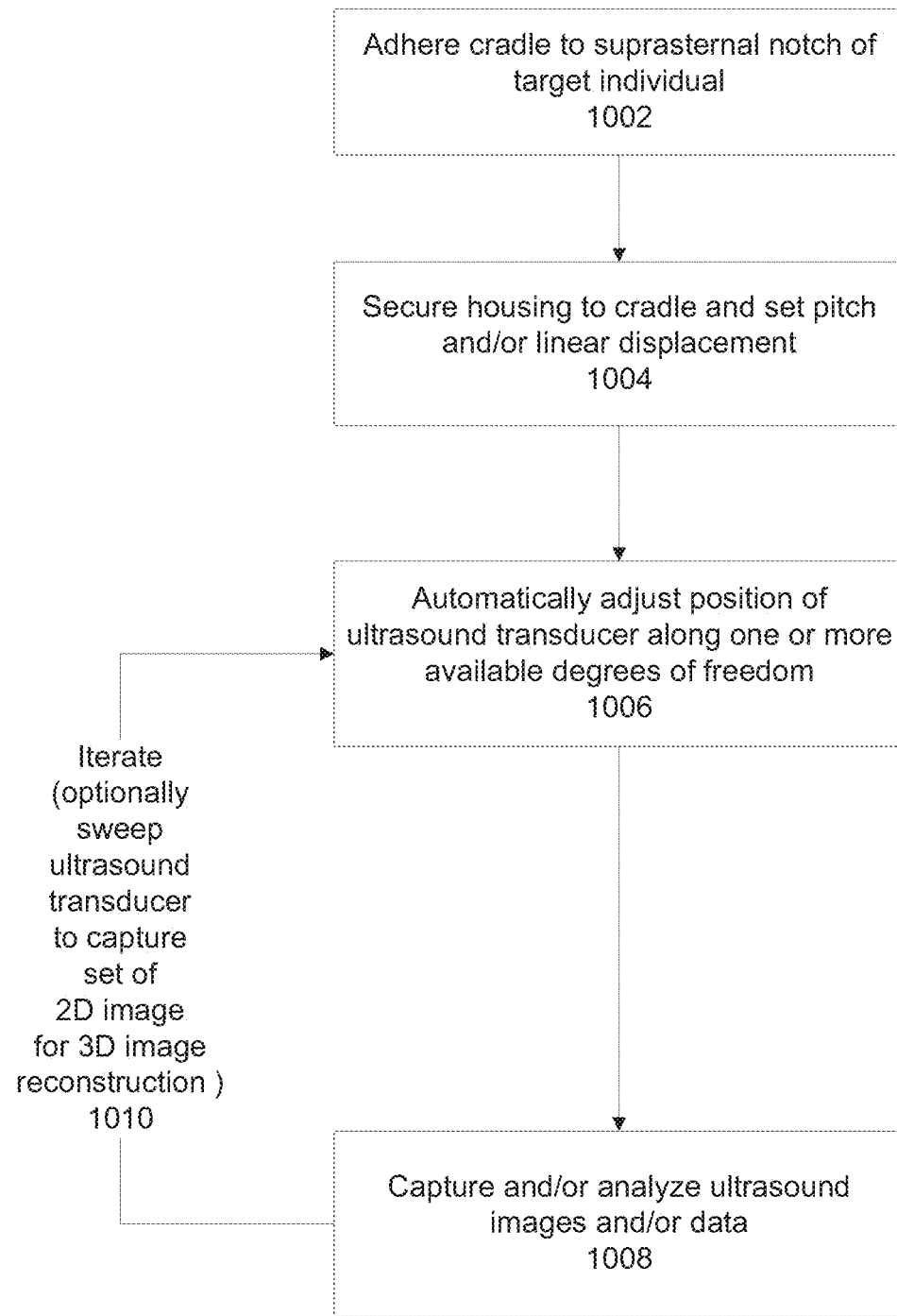
FIG. 10 is a flowchart of a process of setting up an assembly for ultrasonic monitoring and/or imaging via a suprasternal notch of a target individual, in accordance with some embodiments of the present invention.

Reference is now made to FIG. 10, which is a flowchart of a process of setting up an assembly for ultrasonic monitoring and/or imaging via a suprasternal notch of a target individual, in accordance with some embodiments of the present invention. The process is based on components described herein. Features of the process described with reference to FIG. 10 may be integrated with, and/or include, and/or be substituted with one or more features, for example, the method for continuous ultrasonic monitoring described with reference to FIG. 3A, the method for ultrasonic continuous hemodynamic monitoring described with reference to FIG. 3B, and/or the method for determination of the flow direction described with reference to FIG. 4.

At 1002, a lower portion of a cradle is adhered to the suprasternal notch and/or nearby anatomical surface of the neck of the target individual. The cradle may include an adhesive surface for adhering to the neck. The cradle may be selected from different available types according to anatomical characteristics of the target individual, and/or a common cradle (i.e., single type) may be selected.

At 1004, a housing component, including an ultrasound transducer stored within a housing, is secured to the cradle via a securing mechanism. A pitch adjustment mechanism and/or a linear motion mechanism are set according to a selected pitch and/or linear displacement of the ultrasound transducer (and/or housing) relative to the suprasternal notch. For example, a screw(s) of the housing is inserted within an elongated slot of the cradle. The housing is positioned with the cradle at a certain pitch and/or displacement. The screw(s) is tightened to secure the set pitch and/or displacement.

The ultrasound transducer is placed in contact with the surface of the suprasternal notch, directly or indirectly via an acoustic medium by selecting the pitch and/or linear displacement. The pitch and/or linear displacement may be selected according to the expected location of the target internal anatomical structures for imaging by the ultrasound transducer via the suprasternal notch.

At 1006, the multi-directional mechanism of the housing component automatically adjusts the position (e.g., rotation, tilt, linear displacement) of the ultrasound transducer along the available degrees of freedom. The adjustment of the ultrasound transducer may be performed dynamically as part of the search for the target internal anatomical structure(s) (e.g., aorta) and/or monitoring of the target internal anatomical structure(s) and/or tracking the motion of the target internal anatomical structure(s), as described herein.

At 1008, ultrasound images and/or data is captured and/or analyzed as part of the ultrasound imaging and/or monitoring process. For example, for continuous ultrasonic monitoring, for ultrasonic continuous hemodynamic monitoring, and/or for determination of the flow direction, as described herein.

At 1010, acts 1006 and/or 1008 may be iterated, for example, the pitch and/or linear displacement of the housing may be re-adjusted, and the automatic adjustment of the position of the ultrasound transducer may commence, for example, when the target internal structure(s) have not been identified, and/or when image quality is not suitable and/or for monitoring different internal structures. The change in position may improve image quality and/or help locate the target internal anatomical structure(s). It is noted that act 1004 may be a manual initialization process performed one time before execution of acts 1006-1010.

The iteration may be performed as a defined sweeping pattern, which sweeps the ultrasound transducer for example anterior-posterior and/or media-lateral over a predefined region, for capturing a sequence of ultrasound images of one or more target images. Each image represents a two dimensional slice at a certain orientation. One or more three dimensional ultrasound images may be reconstructed from the two dimensional slice images captured according to the sweeping pattern. The 3D ultrasound image(s) may be reconstructed according the position and/or orientation of the ultrasound transducer for each of the two dimensional US image slices. The position and/or orientation may be computed based on setting of the multi-directional mechanism.

Different embodiments are disclosed herein. Features of certain embodiments may be combined with features of other embodiments; thus certain embodiments may be combinations of features of multiple embodiments. The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. An assembly for hands-free ultrasonic monitoring and imaging of at least one target anatomical structure via a suprasternal notch of a target individual, comprising:
   (A) a cradle comprising:
      (i) a lower portion having a surface shaped according to a surface of an anatomical region including a suprasternal notch of at least one sample individual; and
      (ii) a holding portion connected to the lower portion, the holding portion shaped to fit a housing component, the holding portion including at least one elongated slot elongated at a predefined angle relative to the surface of the lower portion; and
   (B) a housing component comprising:
      (i) an ultrasound transducer;
      (ii) a multi-directional mechanism for adjusting the position of the ultrasound transducer within the housing component along at least two degrees of freedom; and
      (iii) a securing mechanism set at a location within housing component for engaging the at least one elongated slot of the cradle when housing component is fitted within the holding portion of the cradle.

2. The assembly according to claim 1, wherein the housing component further comprises:
   (iv) a pitch adjustment mechanism for adjusting a pitch of the housing component relative to the cradle, wherein the securing mechanism locks the housing component at a certain pitch; and
   (v) a linear motion mechanism for adjusting a linear displacement of the housing component relative to the cradle along a linear displacement axis defined along the elongated slot.

3. The assembly according to claim 1, wherein the holding portion of the cradle is sized for providing: (i) a pitch range of the housing component above a baseline pitch substantially corresponding to a pitch of the suprasternal notch when the cradle houses the housing component in use, and (ii) a linear displacement range of motion of the housing component along a linear displacement axis of the holding portion.

4. The assembly according to claim 1, wherein the pitch adjustment mechanism, the linear motion mechanism, and the securing mechanism are implemented by the elongated slot of the cradle and at least one securing element located on one or both of the sides of the housing component, wherein when the at least one securing element is tightened within the at least one elongated slot the housing component is secured within the cradle at the certain pitch and the certain linear displacement.

5. The assembly according to claim 1, wherein the pitch adjustment mechanism is set for adjusting the pitch of the housing component relative to the lower surface of the lower component of the cradle.

6. The assembly according to claim 1, wherein the multi-directional mechanism includes at least one resilient element set for providing linear motion of the ultrasound transducer along a vertical axis of the housing component.

7. The assembly according to claim 6, wherein the at least one resilient element is set for pressing the ultrasound transducer within a compartment housing acoustic transmission material such that the ultrasound transducer maintains contact with the surface of the compartment housing acoustic transmission material during motion within the at least three degrees of motion provided by the multi-directional mechanism.

8. The assembly according to claim 1, wherein the multi-directional mechanism includes a tilting actuator for tiling the ultrasound transducer along a roll axis arranged in parallel to a longitudinal axis of the housing compartment.

9. The assembly according to claim 8, wherein the tilting actuator is located on a bottom surface of a flat plate, wherein the top surface of the flat plate is connected to one end of at least one resilient element of the multi-directional mechanism, wherein an opposite end of the at least one resilient element is coupled to the housing, wherein the at least one resilient element linearly urges the flat plate and connected tilting actuator along a vertical axis of the housing component.

10. The assembly according to claim 1, wherein the multi-directional mechanism includes a rotation actuator for rotating the ultrasound transducer along a yaw axis arranged in parallel to a vertical axis of the housing component.

11. The assembly according to claim 1, wherein the rotation actuator is located on a top surface of a flat plate, wherein the top surface of the flat plate is connected to one end of at least one resilient element of the multi-directional mechanism, wherein an opposite end of the at least one resilient element is coupled to the housing, wherein the at least one resilient element linearly urges the flat plate and connected rotation actuator along a vertical axis of the housing component.

12. The assembly according to claim 11, wherein a rotational motor shaft extends through the flat plate to connect to the support of the ultrasound transducer.

13. The assembly according to claim 1, further comprising a set of a fixed photodiode gate and a needle defining a reference zero position for calibrating each axis of motion of the assembly, wherein motion occurring along each axis of motion is relative to the reference zero point.

14. The assembly according to claim 1, wherein the predefined angle substantially corresponds to an angle between the surface of the suprasternal notch of at least one sample individual and an angle for imaging at least one internal anatomical structure of the at least one sample individual via the suprasternal notch.

15. The assembly according to claim 1, further comprising at least one hardware processor coupled to the multi-directional mechanism and to a data storage device storing code for execution by the at least one hardware processor, the code including instructions for controlling the multi-directional mechanism to perform a defined sweeping pattern that sweeps the ultrasound transducer for capturing a sequence of ultrasound images each representing a two dimensional slice at a certain orientation, wherein at least one three-dimensional image is reconstructed from the sequence of two dimensional ultrasound image slices and according a position and orientation of the ultrasound transducer for each two dimensional slice based on setting of the multi-directional mechanism.

16. The assembly according to claim 1, further comprising at least one handle located on the exterior surface of the cradle, the at least one handle including a strap locking mechanism that secures a strap wrapped around the neck of the patient.

17. A multi-directional mechanism for adjusting a position of an ultrasound transducer within a housing component along at least two degrees of freedom, comprising:
(i) at least one resilient element set for providing linear motion of the ultrasound transducer along a vertical axis of the housing component,
wherein a first end portion of the at least one resilient element is connected to the housing component and a second end portion of the at least one resilient element is connected to the ultrasound transducer;
(ii) a tilting actuator for tiling the ultrasound transducer along a roll axis arranged in parallel to a longitudinal axis of the housing compartment,
(iii) a rotation actuator for rotating the ultrasound transducer along a yaw axis arranged in parallel to a vertical axis of the housing component,
wherein the at least one resilient element linearly urges the tilting actuator and rotation actuator along a vertical axis of the housing component,
wherein the rotation actuator includes a rotation micro stepper motor coupled to a first end portion of a motor shaft, wherein a second end portion of the motor shaft is coupled to a worm gear, wherein the rotation micro stepper motor, the motor shaft, and the worm gear are arranged along a linear axis substantially parallel to a longitudinal axis of the housing component, wherein the worm gear is meshed to a gear of a rotational shaft coupled to a support of the ultrasound transducer, wherein the rotational shaft is arranged substantially parallel to a vertical axis of the housing component, wherein the rotational shaft extends through the flat plate to connect to the support of the ultrasound transducer.

18. The multi-directional mechanism according to claim 17, wherein the gear of the rotational shaft is located along a longitudinal mid-line of the housing component, wherein the rotation micro stepper motor, the motor shaft, and the worm gear are aligned along a longitudinal axis of the housing component located in parallel to the mid-line.

19. The multi-directional mechanism according to claim 17, wherein the rotation actuator is designed for providing a toque sufficient to overcome frictional forces when rotating the ultrasound transducer when the ultrasound transducer is urged by at least one resilient element, the torque selected to overcome frictional forces between the ultrasound transducer and a compartment of an acoustic material.

* * * * *